(12) United States Patent
Cherevatsky et al.

(10) Patent No.: US 9,324,145 B1
(45) Date of Patent: Apr. 26, 2016

(54) SYSTEM AND METHOD FOR DETECTION OF TRANSITIONS IN AN IMAGE STREAM OF THE GASTROINTESTINAL TRACT

(71) Applicant: GIVEN IMAGING LTD., Yoqneam (IL)

(72) Inventors: Boris Cherevatsky, Nesher (IL); Dori Peleg, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 0 days.

(21) Appl. No.: 14/454,975

(22) Filed: Aug. 8, 2014

Related U.S. Application Data

(60) Provisional application No. 61/863,640, filed on Aug. 8, 2013.

(51) Int. Cl.
| | |
|---|---|
| *G06T 7/00* | (2006.01) |
| *A61B 1/04* | (2006.01) |
| *A61B 5/06* | (2006.01) |
| *A61B 19/00* | (2006.01) |
| *G06K 9/00* | (2006.01) |

(52) U.S. Cl.
CPC .............. *G06T 7/0016* (2013.01); *A61B 1/041* (2013.01); *A61B 5/066* (2013.01); *A61B 19/5244* (2013.01); *G06K 9/00147* (2013.01); *G06K 2209/05* (2013.01); *G06T 2207/10016* (2013.01); *G06T 2207/30028* (2013.01)

(58) Field of Classification Search
None
See application file for complete search history.

(56) References Cited

U.S. PATENT DOCUMENTS

| | | | |
|---|---|---|---|
| 3,683,389 | A | 8/1972 | Hollis |
| 3,909,792 | A | 9/1975 | Harris et al. |
| 3,971,362 | A | 7/1976 | Pope et al. |
| 4,017,261 | A | 4/1977 | Svoboda et al. |

(Continued)

FOREIGN PATENT DOCUMENTS

| | | |
|---|---|---|
| CN | 1427692 | 7/2003 |
| CN | 1509152 | 6/2004 |

(Continued)

OTHER PUBLICATIONS

U.S. Appl. No. 13/116,447, filed May 26, 2011, Zingman, Igor et al.

(Continued)

*Primary Examiner* — Utpal Shah
(74) *Attorney, Agent, or Firm* — Pearl Cohen Zedek Latzer Baratz LLP

(57) ABSTRACT

A system and method for detecting a transition in a stream of images of a gastrointestinal (GI) tract may include selecting images from an in-vivo image stream; calculating a segment score for each selected image indicating in which segment of the GI tract the image was captured; applying a smoothing function on the scores; detecting a global step in the smoothed segment score signal indicating a substantial change in a parameter calculated based on segment score signal values of the segment score signal values; detecting a local step indicating a substantial change in a parameter calculated based on segment score signal values of a predetermined interval of the of the segment score signal values; combining the local step and the global step; and determining a point of transition in the stream from one anatomical segment to another, the point of transition correlating to the combined step.

20 Claims, 19 Drawing Sheets
(11 of 19 Drawing Sheet(s) Filed in Color)

(56) References Cited

U.S. PATENT DOCUMENTS

| | | | |
|---|---|---|---|
| 4,278,077 A | 7/1981 | Mizumoto |
| 4,337,222 A | 6/1982 | Kitajima et al. |
| 4,646,724 A | 3/1987 | Sato et al. |
| 4,689,621 A | 8/1987 | Kleinberg |
| 4,698,664 A | 10/1987 | Nichols et al. |
| 4,741,327 A | 5/1988 | Yabe |
| 4,844,076 A | 7/1989 | Lesho et al. |
| 4,854,328 A | 8/1989 | Pollack |
| 4,907,095 A | 3/1990 | Komura et al. |
| 4,920,045 A | 4/1990 | Okuda et al. |
| 4,936,823 A | 6/1990 | Colvin et al. |
| 5,042,494 A | 8/1991 | Alfano |
| 5,187,572 A | 2/1993 | Nakamura et al. |
| 5,209,220 A | 5/1993 | Hiyama et al. |
| 5,212,637 A | 5/1993 | Saxena |
| 5,267,033 A | 11/1993 | Hoshino |
| 5,279,607 A | 1/1994 | Schentag et al. |
| 5,331,551 A | 7/1994 | Tsuruoka et al. |
| 5,333,244 A | 7/1994 | Harashima |
| 5,392,072 A | 2/1995 | Rodriguez et al. |
| 5,494,032 A | 2/1996 | Robinson et al. |
| 5,495,114 A | 2/1996 | Adair |
| 5,519,828 A | 5/1996 | Rayner |
| 5,566,169 A | 10/1996 | Rangan et al. |
| 5,572,252 A | 11/1996 | Naka et al. |
| 5,596,366 A | 1/1997 | Takashima et al. |
| 5,604,531 A | 2/1997 | Iddan et al. |
| 5,605,153 A | 2/1997 | Fujioka et al. |
| 5,647,368 A | 7/1997 | Zeng et al. |
| 5,649,021 A | 7/1997 | Matey et al. |
| 5,697,384 A | 12/1997 | Miyawaki et al. |
| 5,697,885 A | 12/1997 | Konomura et al. |
| 5,726,670 A | 3/1998 | Tabata et al. |
| 5,738,110 A | 4/1998 | Beal et al. |
| 5,819,736 A | 10/1998 | Avny et al. |
| 5,827,190 A | 10/1998 | Palcic Branko et al. |
| 5,830,141 A | 11/1998 | Makram-Ebeid et al. |
| 5,833,603 A | 11/1998 | Kovacs et al. |
| 5,873,830 A | 2/1999 | Hossack et al. |
| 5,880,777 A | 3/1999 | Savoye et al. |
| 5,886,353 A | 3/1999 | Spivey et al. |
| 5,929,901 A | 7/1999 | Adair et al. |
| 5,970,173 A | 10/1999 | Lee et al. |
| 5,986,693 A | 11/1999 | Adair et al. |
| 5,993,378 A | 11/1999 | Lemelson |
| 6,043,839 A | 3/2000 | Adair et al. |
| 6,053,873 A | 4/2000 | Govari et al. |
| 6,095,989 A | 8/2000 | Hay et al. |
| 6,097,399 A | 8/2000 | Bhatt et al. |
| 6,106,457 A | 8/2000 | Perkins et al. |
| 6,117,529 A | 9/2000 | Leising et al. |
| 6,157,677 A | 12/2000 | Martens et al. |
| 6,166,496 A | 12/2000 | Lys et al. |
| 6,188,403 B1 | 2/2001 | Sacerdoti et al. |
| 6,222,547 B1 | 4/2001 | Schwuttke et al. |
| 6,240,312 B1 | 5/2001 | Alfano et al. |
| 6,289,165 B1 | 9/2001 | Abecassis |
| 6,335,736 B1 | 1/2002 | Wagner et al. |
| 6,339,446 B1 | 1/2002 | Miyoshi |
| 6,402,689 B1 | 6/2002 | Scarantino et al. |
| 6,428,469 B1 | 8/2002 | Iddan et al. |
| 6,459,919 B1 | 10/2002 | Lys et al. |
| 6,504,990 B1 | 1/2003 | Abecssis |
| 6,614,452 B1 | 9/2003 | Caleb |
| 6,632,175 B1 | 10/2003 | Marshall |
| 6,635,834 B1 | 10/2003 | Wenner |
| 6,654,504 B2 | 11/2003 | Lubin et al. |
| 6,709,387 B1 | 3/2004 | Glukhovsky et al. |
| 6,757,412 B1 | 6/2004 | Parsons et al. |
| 6,791,601 B1 | 9/2004 | Chang et al. |
| 6,900,790 B1 | 5/2005 | Doi et al. |
| 6,904,308 B2 | 6/2005 | Frisch et al. |
| 6,939,292 B2 | 9/2005 | Mizuno |
| 6,944,316 B2 | 9/2005 | Glukhovsky et al. |
| 6,947,788 B2 | 9/2005 | Gilboa et al. |
| 6,950,690 B1 | 9/2005 | Meron et al. |
| 6,976,229 B1 | 12/2005 | Balabanovic et al. |
| 6,984,205 B2 | 1/2006 | Gazdzinski |
| 7,009,634 B2 | 3/2006 | Iddan et al. |
| 7,022,067 B2 | 4/2006 | Glukhovsky et al. |
| 7,039,453 B2 | 5/2006 | Mullick et al. |
| 7,083,578 B2 | 8/2006 | Lewkowicz et al. |
| 7,112,752 B1 | 9/2006 | Wenner |
| 7,119,814 B2 | 10/2006 | Meron et al. |
| 7,136,518 B2 | 11/2006 | Griffin et al. |
| 7,190,818 B2 | 3/2007 | Ellis et al. |
| 7,215,338 B2 | 5/2007 | Horn et al. |
| 7,219,034 B2 | 5/2007 | McGee et al. |
| 7,221,388 B2 | 5/2007 | Yamazaki et al. |
| 7,228,166 B1 | 6/2007 | Kawasaki et al. |
| 7,232,410 B2 | 6/2007 | Takahashi |
| 7,236,623 B2 | 6/2007 | Chapoulaud et al. |
| 7,245,746 B2 | 7/2007 | Bjaerum et al. |
| 7,251,383 B2 | 7/2007 | Iddan |
| 7,260,777 B2 | 8/2007 | Fitzsimons et al. |
| 7,272,657 B2 | 9/2007 | Allen et al. |
| 7,287,105 B1 | 10/2007 | Owen et al. |
| 7,295,226 B1 | 11/2007 | Meron et al. |
| 7,316,647 B2 | 1/2008 | Kimoto et al. |
| 7,319,781 B2 | 1/2008 | Chen et al. |
| 7,324,673 B1 | 1/2008 | Yamanaka et al. |
| 7,452,328 B2 | 11/2008 | Homan et al. |
| 7,567,692 B2 | 7/2009 | Buzaglo et al. |
| 7,636,092 B2 | 12/2009 | Horn et al. |
| 7,672,497 B2 | 3/2010 | Nicponski |
| 7,684,599 B2 | 3/2010 | Horn et al. |
| 7,694,320 B1 | 4/2010 | Yeo et al. |
| 7,885,446 B2 | 2/2011 | Horn et al. |
| 7,953,261 B2 | 5/2011 | Nishimura et al. |
| 7,970,455 B2 | 6/2011 | Zilberstein et al. |
| 7,986,337 B2 | 7/2011 | Davidson et al. |
| 8,144,152 B2 | 3/2012 | Horn et al. |
| 8,164,672 B2 * | 4/2012 | Meron .............. H04N 7/181 348/333.05 |
| 8,768,024 B1 * | 7/2014 | Zingman ............ G06T 5/30 348/45 |
| 8,873,816 B1 | 10/2014 | Dori et al. |
| 8,911,360 B2 | 12/2014 | Khait et al. |
| 8,922,633 B1 | 12/2014 | Pfeffer |
| 8,965,079 B1 | 2/2015 | Zinaty et al. |
| 2001/0035902 A1 | 11/2001 | Iddan et al. |
| 2001/0051766 A1 | 12/2001 | Gazdzinski |
| 2002/0042562 A1 | 4/2002 | Meron et al. |
| 2002/0103417 A1 | 8/2002 | Gazdzinski |
| 2002/0103425 A1 | 8/2002 | Mault |
| 2002/0132226 A1 | 9/2002 | Nair et al. |
| 2002/0140861 A1 | 10/2002 | Janevski et al. |
| 2002/0173718 A1 | 11/2002 | Frisch et al. |
| 2002/0177779 A1 | 11/2002 | Adler et al. |
| 2002/0186234 A1 | 12/2002 | Van de Streek et al. |
| 2002/0193669 A1 | 12/2002 | Glukhovsky |
| 2002/0198439 A1 | 12/2002 | Mizuno |
| 2003/0016864 A1 | 1/2003 | McGee et al. |
| 2003/0020810 A1 | 1/2003 | Takizawa et al. |
| 2003/0063130 A1 | 4/2003 | Barbieri et al. |
| 2003/0077223 A1 | 4/2003 | Glukhovsky et al. |
| 2003/0086596 A1 | 5/2003 | Hipp et al. |
| 2003/0142753 A1 | 7/2003 | Gunday |
| 2003/0151661 A1 | 8/2003 | Davidson et al. |
| 2003/0167000 A1 | 9/2003 | Mullick et al. |
| 2003/0174208 A1 | 9/2003 | Glukhovsky et al. |
| 2003/0208107 A1 | 11/2003 | Refael |
| 2004/0010375 A1 | 1/2004 | Schomacker et al. |
| 2004/0027500 A1 | 2/2004 | Davidson et al. |
| 2004/0066398 A1 | 4/2004 | Dolimier et al. |
| 2004/0073087 A1 | 4/2004 | Glukhovsky et al. |
| 2004/0111011 A1 | 6/2004 | Uchiyama et al. |
| 2004/0115877 A1 | 6/2004 | Iddan |
| 2004/0180391 A1 | 9/2004 | Gratzl et al. |
| 2004/0184639 A1 | 9/2004 | Jackson et al. |
| 2004/0196287 A1 | 10/2004 | Wong et al. |
| 2004/0225223 A1 | 11/2004 | Honda et al. |
| 2004/0249291 A1 | 12/2004 | Honda et al. |
| 2004/0257620 A1 | 12/2004 | Loce et al. |

(56) References Cited

U.S. PATENT DOCUMENTS

| | | |
|---|---|---|
| 2004/0264754 A1 | 12/2004 | Kleen et al. |
| 2004/0279291 | 12/2004 | Honda et al. |
| 2005/0007551 A1 | 1/2005 | Wakil et al. |
| 2005/0065421 A1 | 3/2005 | Burckhardt |
| 2005/0074151 A1 | 4/2005 | Chen et al. |
| 2005/0075537 A1 | 4/2005 | Chen et al. |
| 2005/0075551 A1 | 4/2005 | Horn et al. |
| 2005/0148816 A1 | 7/2005 | Glukhovsky et al. |
| 2005/0152588 A1 | 7/2005 | Yoshida et al. |
| 2005/0171418 A1 | 8/2005 | Lin |
| 2005/0196023 A1 | 9/2005 | Chen et al. |
| 2005/0215876 A1 | 9/2005 | Chen et al. |
| 2005/0228293 A1 | 10/2005 | Cahill et al. |
| 2005/0259854 A1 | 11/2005 | Arimura et al. |
| 2005/0266074 A1 | 12/2005 | Zilberstein et al. |
| 2005/0281446 A1 | 12/2005 | Glukhovsky et al. |
| 2005/0288594 A1 | 12/2005 | Lewkowicz et al. |
| 2006/0050966 A1 | 3/2006 | Nishimura et al. |
| 2006/0069317 A1* | 3/2006 | Horn ............... A61B 5/065 600/300 |
| 2006/0074275 A1 | 4/2006 | Davidson et al. |
| 2006/0155174 A1 | 7/2006 | Glukhovsky et al. |
| 2006/0164511 A1 | 7/2006 | Krupnik |
| 2006/0187300 A1 | 8/2006 | Davidson |
| 2006/0193505 A1 | 8/2006 | Glukhovsky et al. |
| 2006/0217593 A1 | 9/2006 | Gilad et al. |
| 2006/0239557 A1 | 10/2006 | Cahill et al. |
| 2007/0053557 A1 | 3/2007 | Cahill et al. |
| 2007/0078335 A1* | 4/2007 | Horn ............... A61B 1/04 600/425 |
| 2007/0104272 A1 | 5/2007 | He et al. |
| 2007/0135715 A1 | 6/2007 | Inoue et al. |
| 2007/0159483 A1 | 7/2007 | Horn et al. |
| 2007/0165924 A1 | 7/2007 | Nicponski |
| 2007/0165932 A1 | 7/2007 | Nishimura et al. |
| 2007/0165942 A1 | 7/2007 | Jin et al. |
| 2007/0230893 A1 | 10/2007 | Meron et al. |
| 2007/0255095 A1* | 11/2007 | Gilreath ............ A61B 1/0005 600/102 |
| 2007/0292011 A1 | 12/2007 | Nishimura et al. |
| 2008/0051642 A1 | 2/2008 | Krupnik |
| 2008/0147087 A1 | 6/2008 | Horn et al. |
| 2008/0242931 A1 | 10/2008 | Nishino |
| 2008/0269664 A1 | 10/2008 | Trovato et al. |
| 2009/0135250 A1 | 5/2009 | Davidson et al. |
| 2009/0148058 A1 | 6/2009 | Dane et al. |
| 2009/0196476 A1 | 8/2009 | Inoue |
| 2009/0306632 A1 | 12/2009 | Trovato et al. |
| 2009/0318761 A1 | 12/2009 | Rabinovitz |
| 2010/0046816 A1* | 2/2010 | Igual-Munoz ........ G06K 9/4623 382/128 |
| 2010/0053313 A1 | 3/2010 | Horn et al. |
| 2010/0166272 A1 | 7/2010 | Horn et al. |
| 2010/0183210 A1 | 7/2010 | Uitert et al. |
| 2010/0189326 A1 | 7/2010 | McGinnis et al. |
| 2011/0033094 A1 | 2/2011 | Zarkh et al. |
| 2011/0164126 A1* | 7/2011 | Ambor ............ A61B 1/0005 348/65 |
| 2011/0206250 A1 | 8/2011 | McGinnis |
| 2011/0243523 A1 | 10/2011 | Davidson et al. |
| 2012/0139936 A1 | 6/2012 | Horn et al. |
| 2013/0304446 A1* | 11/2013 | Rabinovitz .......... G06F 19/12 703/11 |

FOREIGN PATENT DOCUMENTS

| | | |
|---|---|---|
| DE | 3440177 | 5/1986 |
| EP | 1618832 | 1/2006 |
| GB | 2 374 149 | 10/2002 |
| GB | 2 374 149 | 10/2002 |
| JP | 57-45833 | 3/1982 |
| JP | 4109927 | 4/1992 |
| JP | 5015515 | 1/1993 |
| JP | 6142081 | 5/1994 |
| JP | 10112835 | 4/1998 |
| JP | 2000/047651 | 2/2000 |
| JP | 2001/37718 | 2/2001 |
| JP | 2003/122805 | 4/2003 |
| JP | 2004/120367 | 4/2004 |
| JP | 2004/521662 | 7/2004 |
| JP | 2004-521693 | 7/2004 |
| JP | 4067407 | 7/2004 |
| JP | 2004/321603 | 11/2004 |
| JP | 2004/337596 | 12/2004 |
| WO | WO 97/33513 | 9/1997 |
| WO | WO 99/30610 | 6/1999 |
| WO | WO 99/40587 | 8/1999 |
| WO | WO 99/60353 | 11/1999 |
| WO | WO 00/22975 | 4/2000 |
| WO | WO 00/58967 | 10/2000 |
| WO | WO 01/06926 | 2/2001 |
| WO | WO 01/65995 | 9/2001 |
| WO | WO 02/26103 | 4/2002 |
| WO | WO 02/073507 | 9/2002 |
| WO | WO 02/082979 | 10/2002 |
| WO | WO 02082979 | 10/2002 |
| WO | WO 02/102221 | 12/2002 |
| WO | WO 02/102223 | 12/2002 |

OTHER PUBLICATIONS

U.S. Appl. No. 13/208,611, filed Aug. 12, 2011, Krupnik, Hagai et al.
U.S. Appl. No. 13/245,273, filed Sep. 26, 2011, Pfeffer, Yehuda.
Office Action issued for U.S. Appl. No. 11/235,541, dated Sep. 8, 2008.
Final Office Action issued for U.S. Appl. No. 11/235,541, dated Feb. 25, 2009.
Notice of Allowance issued by the United States Patent and Trademark Office for U.S. Appl. No. 11/235,541, dated Aug. 21, 2009.
Notice of Allowance issued by the United States Patent and Trademark Office for U.S. Appl. No. 11/235,541, dated Dec. 30, 2009.
Office Action issued for U.S. Appl. No. 10/493,751, dated Apr. 20, 2007.
Office Action issued for U.S. Appl. No. 10/493,751, dated Oct. 18, 2007.
Office Action issued for U.S. Appl. No. 10/493,751, dated Mar. 26, 2008.
Office Action issued for U.S. Appl. No. 10/493,751, dated Mar. 18, 2009.
Office Action issued for U.S. Appl. No. 10/493,751, dated Aug. 13, 2009.
Office Action issued for U.S. Appl. No. 10/493,751, dated Mar. 12, 2010.
Berens et al., "Stomach, Intestine and Colon Tissue Discriminators for Wireless Capsule Endoscopy Images", Proc of SPIE, vol. 5747, pp. 283-290, 2005.
Office Action issued for U.S. Appl. No. 12/719,601, dated Jun. 22, 2010.
Notice of Allowance issued by the United States Patent and Trademark Office for U.S. Appl. No. 12/719,601, dated Oct. 7, 2010.
Office Action issued for U.S. Appl. No. 12/543,977, dated Apr. 16, 2012.
Office Action issued for U.S. Appl. No. 12/543,977, dated Aug. 23, 2012.
Igual et al., "Automatic Discrimination of Duodenum in Wireless Capsule Video Endoscopy", 2009, 4th European Conference of the International Federation for Medical and Biological Engineering, IFMBE Proceedings vol. 22, pp. 1536-1539.
Bashar et al. "Automatic detection of informative frames from wireless capsule endoscopy images," Jan. 4, 2010, Medical Image Analysis 14,) 449-470.
Notice of Allowance issued by the United States Patent and Trademark Office for U.S. Appl. No. 13/907,076, dated Feb. 27, 2014.
Office Action issued for U.S. Appl. No. 13/907,076, dated Oct. 3, 2013.
Medscape Gastroenterology, "A Mosaic Pattern of the Descending Duodenum," Medscape Gastroenterology 2(1), 2000. http://www.medscape.com/viewarticle/405488_2, retrieved Jun. 2, 2008.
Video Camera to "TAKE"—RF System Lab, Dec. 25, 2001.

(56) References Cited

OTHER PUBLICATIONS

Crum A. "Wellesley Company Sends Body Montiors into Space" Boston Business Journal, Apr. 1998.

Swain et al. "Wireless Transmission of a color television moving image from the stomach using a miniature CCD camera, light source and microwave transmitter" Gastrointest Endosc, 45:AB40, 1997.

BBC News Online—"Pill Camera to 'Broadcast from the Gut'"www.news.bbc.co.uk, Feb. 21, 2000.

Davis E.R "Machine Vision: Theory, Algorithms, Practicalities" $3^{rd}$ Edition, Sep. 2005.

Tagare et al. "Non-Lambertian Shading and Photometric Stereo" SPIE vol. 1260 Sensing and Reconstruction of Three-Dimensional Object Scenes, 1990.

Lee et al. "Robust Shape Reconstruction from Combined Shading and Stereo Information" SPIE vol. 1771 Applications of Digital Image Processing XV, pp. 171-182, 1992.

Powell et al. "Shedding Light on Cancer Diagnosis" Powell (Ed.), Laser Focus World pp. 1-11, May 2000.

Russel et al. "Simulation of Images by Photometric Stereo Modeling" Optical Engineering (ISSN 0091-3286), vol. 30, pp. 1337-1346. Research supported by DND, 1991.

Yang et al. "Two-Image Photometric Stereo Method" SPIE vol. 1826, pp. 452-463, Intelligent Robots and Computer Vision XI , 1992.

www.oceanoptics.com- pH Sensor & Accessories, © 2001.

Hirata et al. "Study of New Prognostic factors of Esophageal Variceal Rupture by Use of Image Processing with a Video Endoscope" Surgery, pp. 8-16, 1994.

Ichikawa et al. "Quantitative Analysis of Red Color Sign in the Endoscopic Evaluation of Esophageal Varices" Endoscopy vol. 33(9) pp. 747-753, 2001.

Frohlich, B. "Exploring Geo-Scientific Data in Virtual Environments" ACM Proc. Conf. on Vis., pp. 169-173, Figs 4-5, Nov. 1999.

Economides et al. "Advances in Production Engineering", Web, http://pumpjack.tamu.edu/-valko/CV/ValkoPDF/CanadianInvpaper.pdf., pp. 1-24, Sep. 11, 2003.

Nuntius et al. "Multimedia Technology, H.264—A New Technology for Video Compression" http://www.nuntius.com/technology3.html, pp. 1-4, Oct. 6, 2006.

Lewis B.S "The Utility of Capsule Endoscopy in Obscure Gastrointestinal Bleeding" Techniques in Gastrointestinal Endoscopy W.B. Saunders, vol. 5, No. 3, pp. 115-120, XP004795573 ISSN: 1096-2883, Jul. 2003.

Davidson et al. "Multi-viewing of Video Streams: A New Concept for Efficient Review of Capsule Endoscopy Studies" Gastrointestinal Endoscopy, vol. 57, No. 5, p. AB164, 2003.

Yoshitaka et al. "Content-Based Retrieval of Video Data by the Grammar of Film" IEEE Symposium on Visual Languages Proceedings, pp. 310-317, Sep. 1997.

Internet Archive Web Shots of Feb. 29, 2000 Weather.com, http://web.archive.org/web/*/http://www.weather.com/, pp. 1-15, Printed on Oct. 21, 2010.

Medscape Gastroenterology, "A Mosaic Pattern of the Descending Duodenum", Medscape Gastroenterology, vol. 2, No. 1, Medscape, <URL:http://www.medscape.com/viewarticle/405488_2>, retrieved Jun. 2, 2008.

Igual et al., "Automatic Discrimination of Duodenum in Wireless Capsule Video Endoscopy", $4^{th}$ European Conference of the International Federation for medical andBiological Engineering, IFMBE Proceedings vol. 22, pp. 1536-1539, 2009.

Bashar et al. "Automatic detection of informative frames from wireless capsule endoscopy images," Jan. 4, 2010, medical Image Analysis 14, pp. 449-470.

Rowlands et al. "The Radio Pill", British Communications and Electronics, Aug. 1960, pp. 598-601.

www.obsltd.co.uk—Data Warehousing Printed on Jan. 22, 2001.

Bruil et al. "In Vivo Leucocyte Adhesion to Modified Polyurethane Surfaces", Biomaterials, vol. 13(13) pp. 915-923, 1992.

* cited by examiner

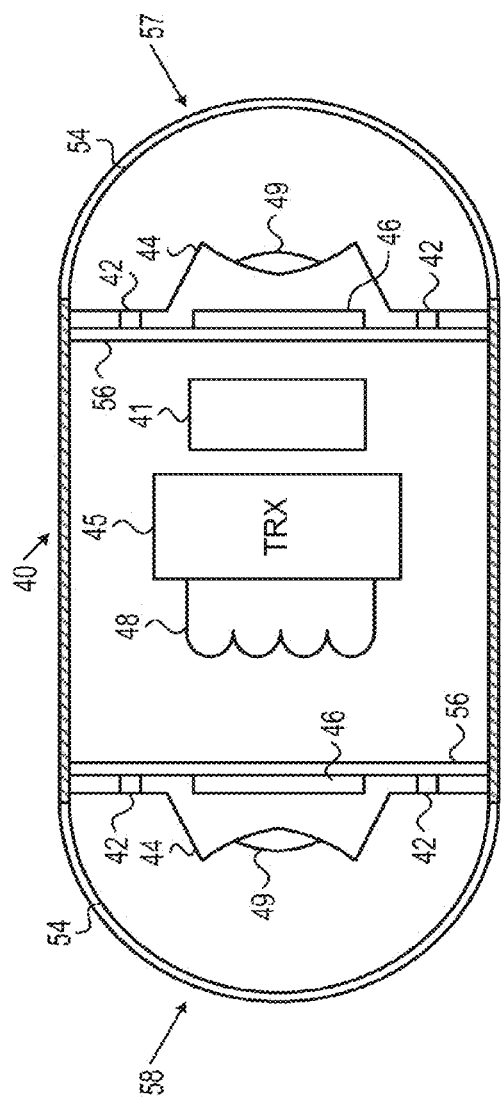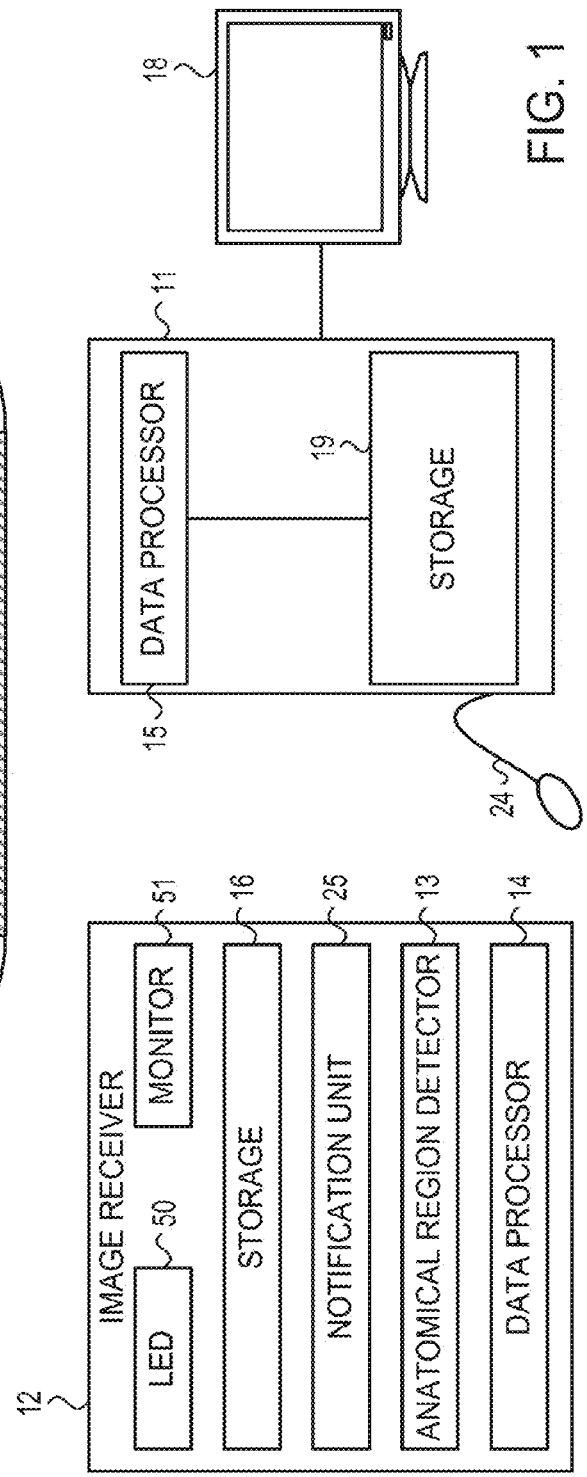
FIG. 1

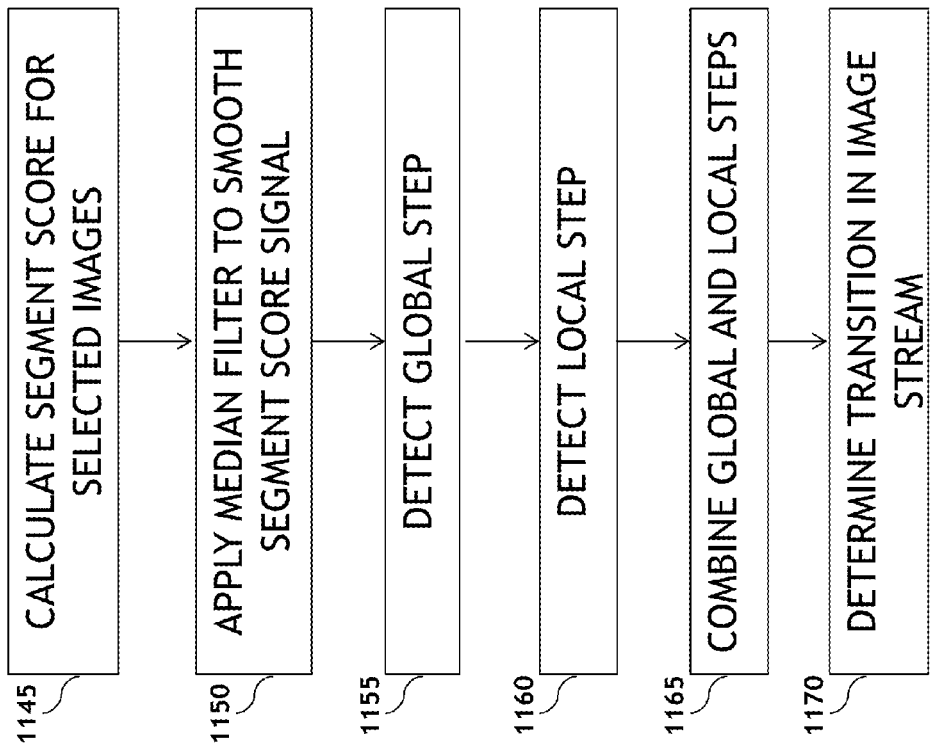

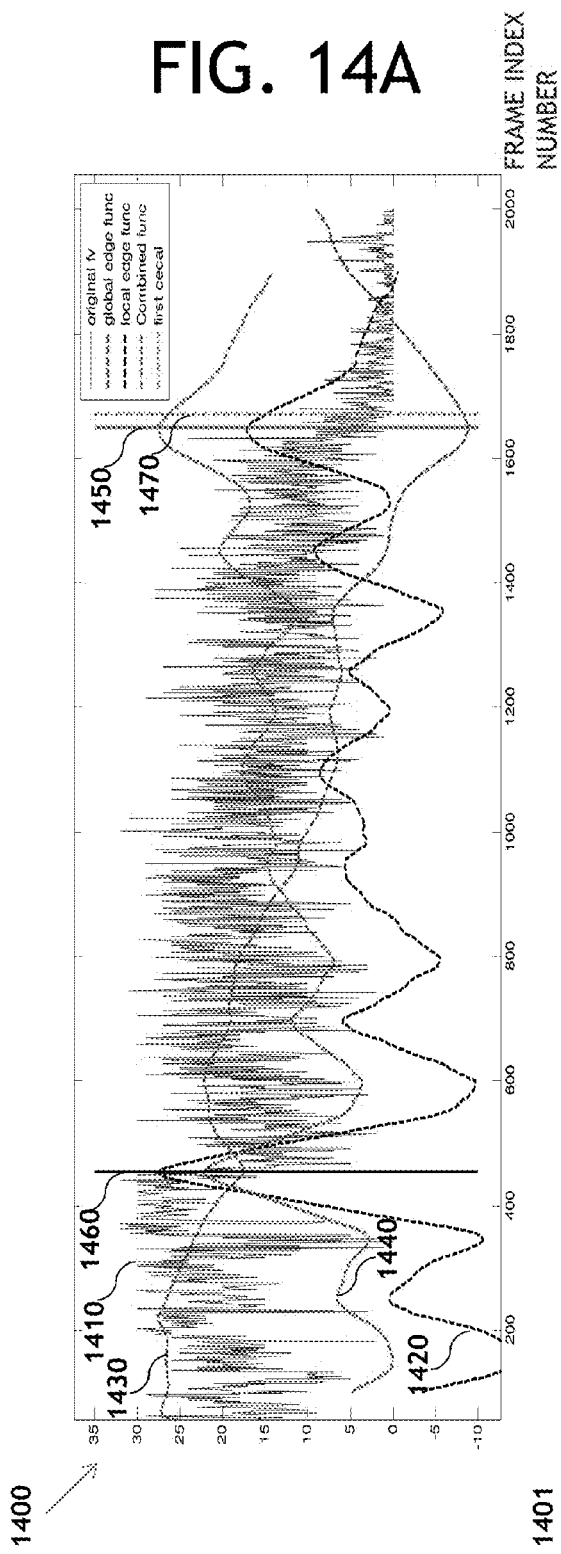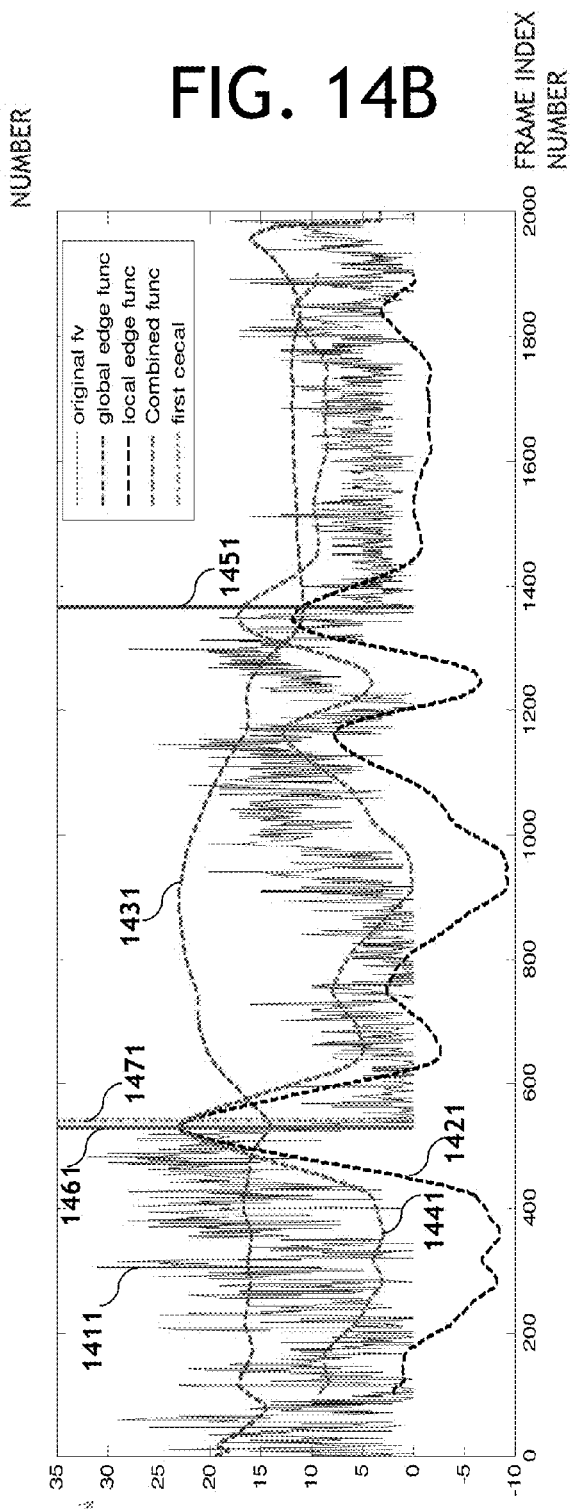

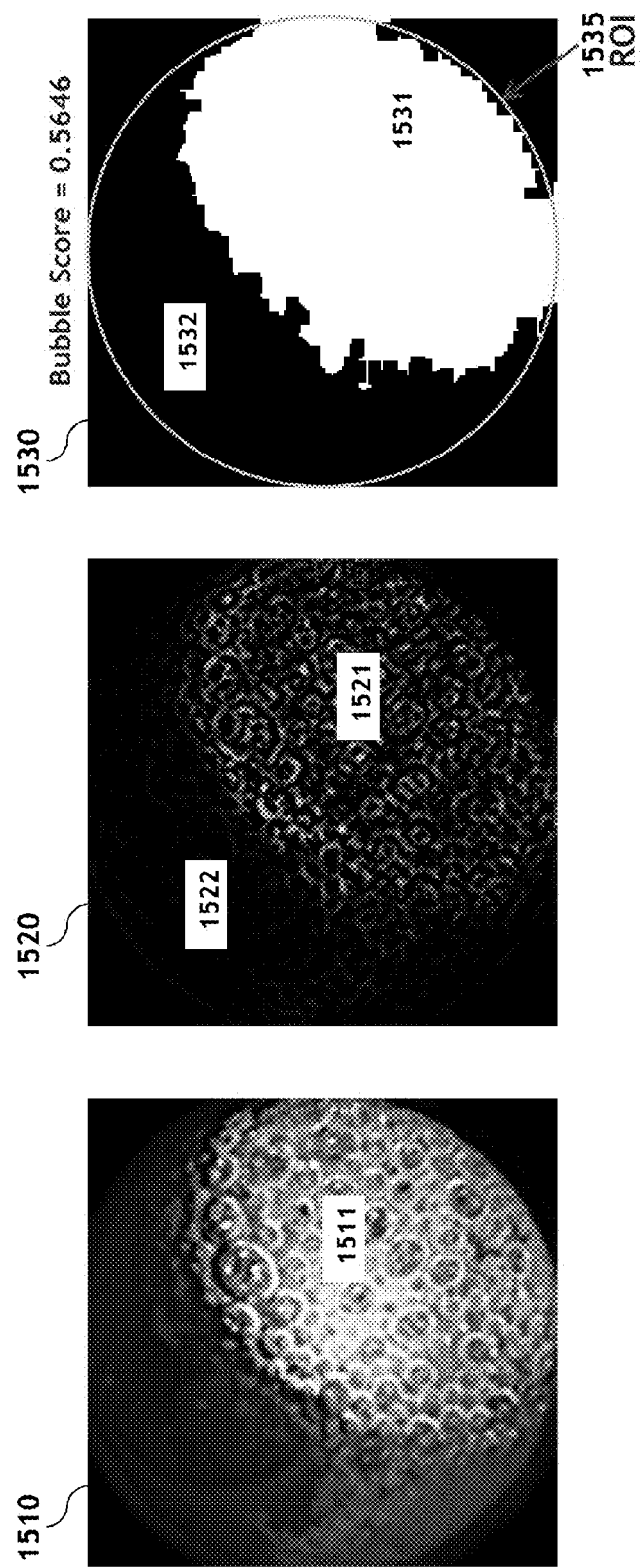

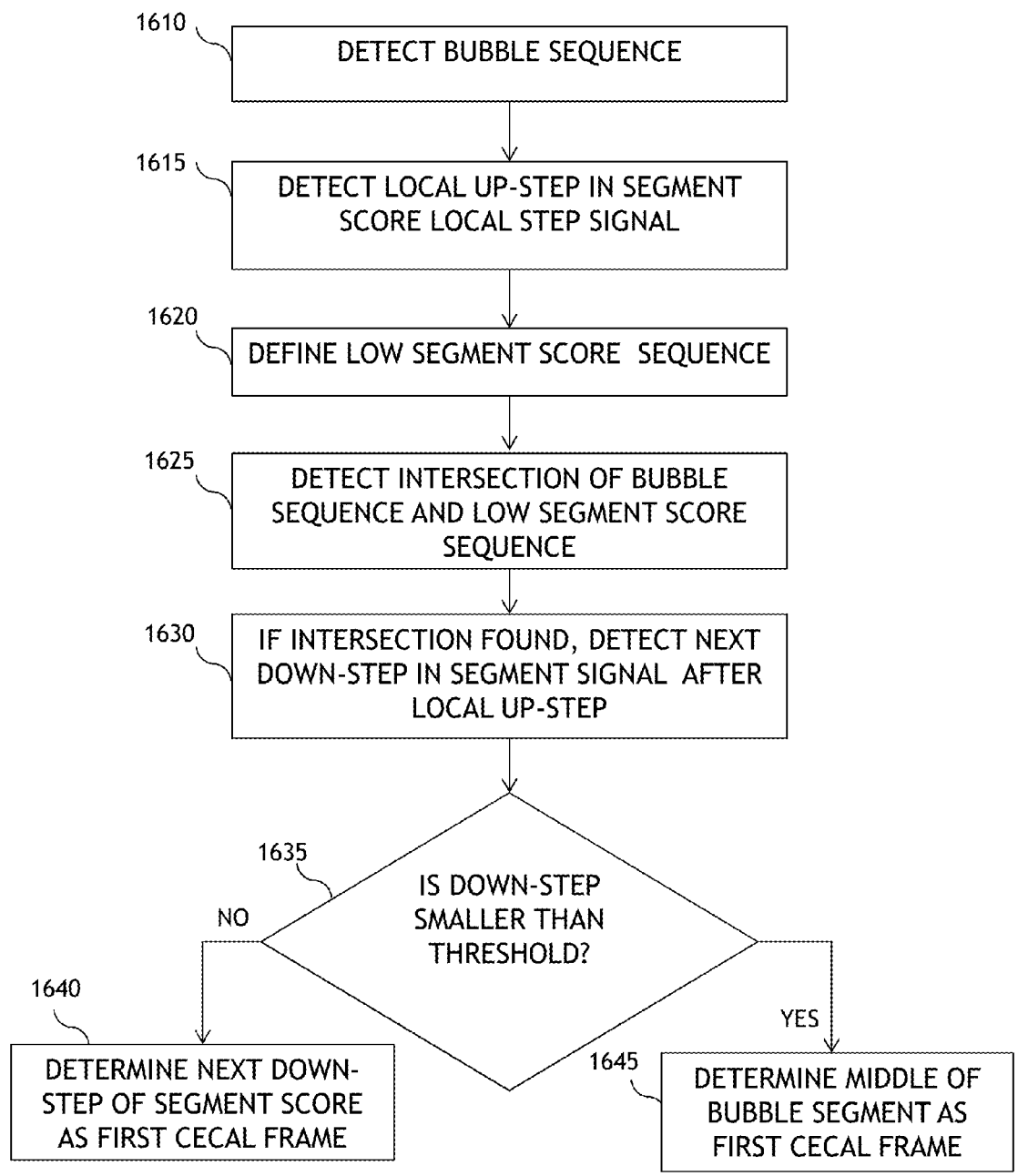

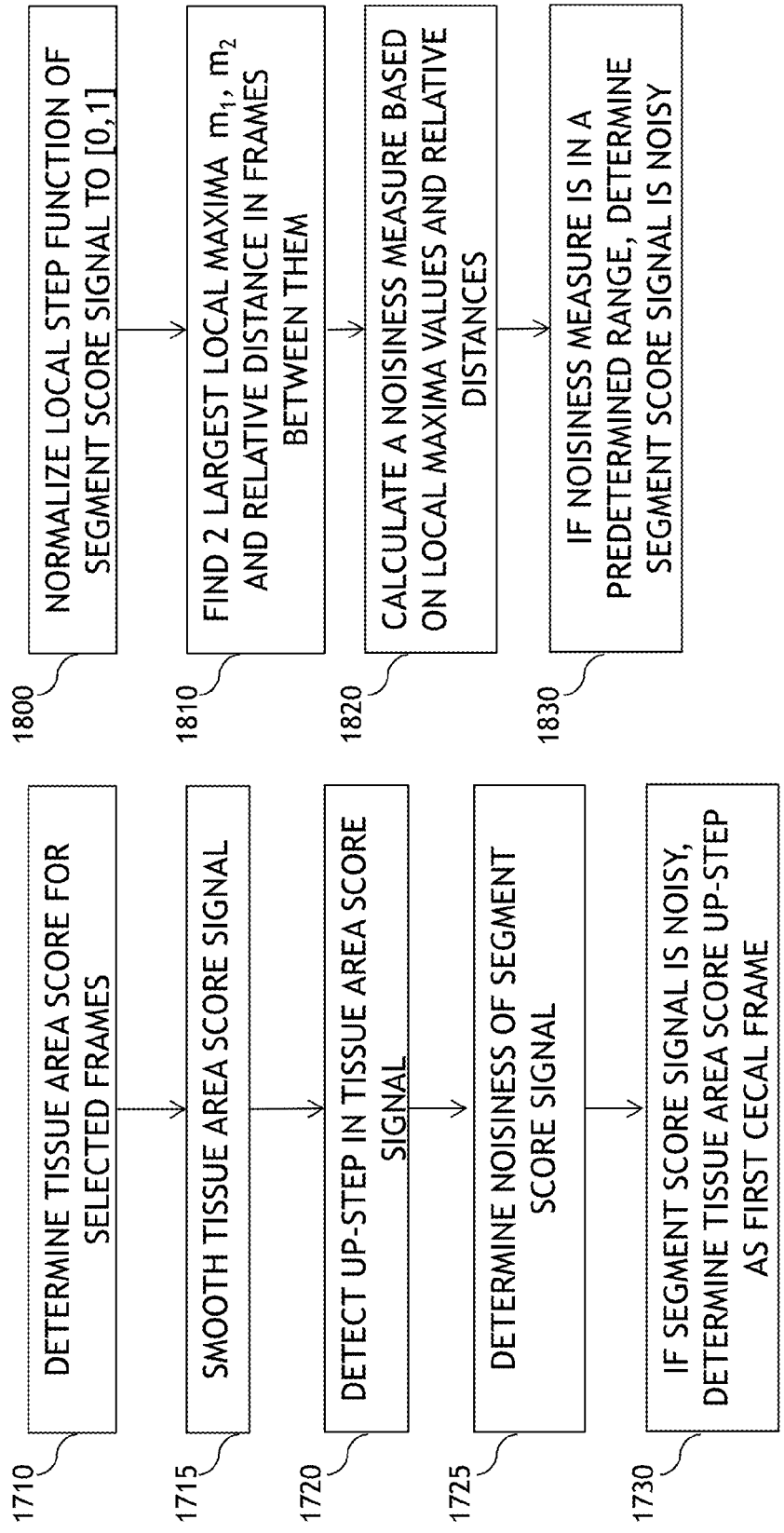

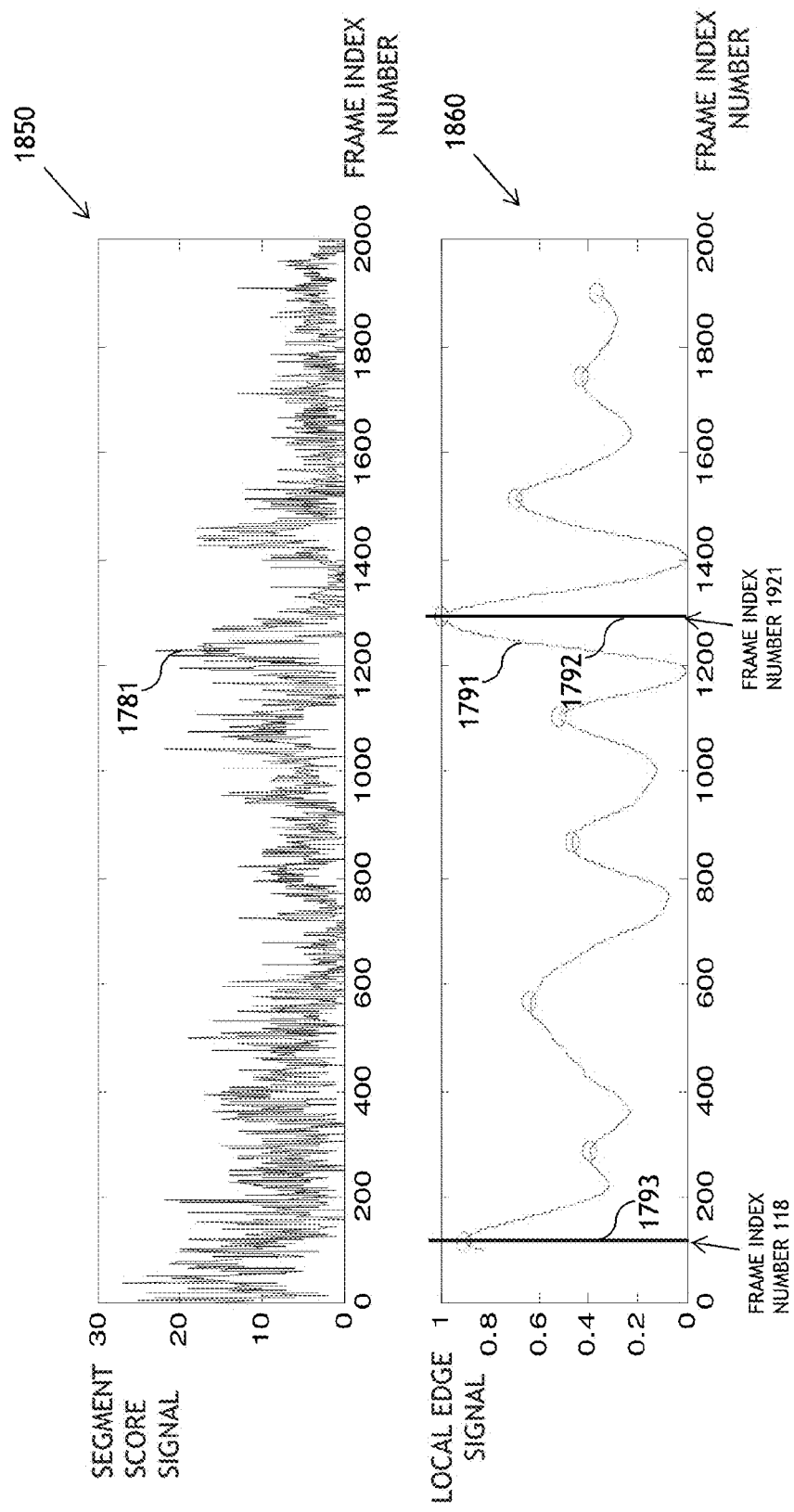

SYSTEM AND METHOD FOR DETECTION OF TRANSITIONS IN AN IMAGE STREAM OF THE GASTROINTESTINAL TRACT

PRIOR APPLICATION DATA

The present application claims benefit from prior provisional application 61/863,640, filed on Aug. 8, 2013, incorporated by reference herein in its entirety.

FIELD OF THE INVENTION

The present invention relates to a method and system for image processing of an image stream captured in-vivo. More specifically, the present invention relates to systems and methods for detecting villi structures in an image stream of the gastrointestinal tract.

BACKGROUND

In-vivo imaging methods, such as performed by an in-vivo imaging system including an ingestible capsule, may be used to image body lumens within a patient. The imaging system may capture and transmit, for example, images of the gastrointestinal (GI) tract to an external recording device, while the capsule passes through the GI lumen. The capsule may capture images in variable frame rates of, for example, 4-40 frames per second. Large numbers of images, for example 100,000 to 300,000 images, may be collected for viewing during the imaging procedure, and may also be viewed and/or processed in real time. The images may be combined in sequence, and an image stream or movie of, for example, 30-120 minutes in length, may be presented to a user.

It would be desirable to provide a user, for example a physician, an indication of the capsule's current position in the body lumen. For example, it may be useful to indicate whether an ingestible capsule is in the stomach or has passed to the small bowel, or whether the capsule entered the colon.

SUMMARY

Embodiments of the invention may include a computer-implemented method for detecting a transition in a stream of in-vivo images of a gastrointestinal (GI) tract. The method may include receiving an in-vivo image stream from an in vivo imaging device, for example a capsule endoscope. A subset of images from the stream may be selected for analysis. A segment score may be calculated for each selected image, the segment score indicating in which anatomic segment of the GI tract the image was captured. A segment score signal, curve or function may be generated, the segment score signal including the segment score values that were calculated for each selected image.

A smoothing function may be applied to the segment score values of the selected images, to obtain a smoothed segment score signal. A global step or increment may be detected in the smoothed segment score signal. The global step may indicate an abrupt or sudden change in a parameter calculated based on the segment score signal values, e.g. a sum or a mean level of the segment score signal values. A local step or increment may be detected in the smoothed segment score signal. The local step may indicate a maximum change or difference, or an abrupt or sudden change in a parameter calculated based on a predetermined interval of the of segment score signal values, e.g. a mean level of a predetermined window, interval or sub-segment of the of the segment score signal values.

In some embodiments, the local step and the global step may be combined to obtain a combined step. A transition in the image stream, e.g. a point in which the imaging device passes from one anatomical segment to another, may be detected in the image stream. The point of transition may correlate to the detected combined step.

A feature vector may be calculated for each selected image, based on, for example, a villi score (the villi score corresponding to an amount of villi texture found in a selected image), a content score (the content score corresponding to the probability that the pixel depicts intestinal contents) and a white score (the white score indicating pixels values which are substantially white).

In some embodiments, a bubble sequence may be detected in the image stream, the bubble sequence corresponding to a sequence of images. Each image of the bubble sequence may contain at least a certain predetermined amount or percentage of bubbles. The point of transition in the image stream, detected based on the combined step, may be corrected according to the detected bubble sequence. The correction may include, for example, determining the middle of the bubble sequence as a corrected point of transition, if there is an overlap or intersection between the bubble sequence and a low segment score sequence. A low segment score sequence, according to embodiments of the invention, may include a sequence of image frames with relatively low segment score values, compared to other frames in the vicinity of the sequence. Detecting the low segment score sequence may include detecting a local step in a local step function of the segment score signal.

The point of transition in the image stream may be, for example, from one anatomical region to another, e.g. from the stomach to the small bowel, and/or from the small bowel to the colon. More than one point of transition between other organs, segments or sub-segments of the GI tract may be detected in an image stream.

In some embodiments, a noisiness level of the segment score signal. The noisiness level may indicate if the segment score signal is reliable for use in determining a point of transition in the image stream. If the noisiness level of the segment score signal is above a predetermined threshold, a tissue area score may be calculated for each selected image to obtain a tissue area score signal, the tissue area score per image indicating an amount of tissue which is captured in an image. A step may be determined in the tissue area score signal, the step indicating a maximum difference, or an abrupt or sudden change in a parameter calculated based on the segment score signal values, e.g. the mean level of tissue score values of sequential images (or sequential selected images). The transition in the image stream may be determined according to the detected step in the tissue area score signal.

In some embodiments, the detected point of transition of the image stream may be refined, for example by selecting a new subset of images from the image stream, the new subset being selected from the vicinity of the detected point of transition.

A system for detecting a transition in a stream of in-vivo images of a gastrointestinal (GI) tract is provided according to embodiments of the invention. The system may include a storage unit to store an in-vivo image stream received from an in vivo imaging device, and a processor to select a subset of images from the stream for analysis. The processor may calculate a segment score for each selected image, the segment score indicating in which anatomic segment of the GI tract the image was captured, and may apply a smoothing function to the segment scores of the selected images to obtain a smoothed segment score signal. The processor may detect a global step in the smoothed segment score signal, said global step indicating an abrupt, conspicuous or substantial change in a parameter calculated based on a predetermined interval of the of the segment score signal values, e.g. a mean level of the segment score signal values. The processor may detect a local step in the smoothed segment score signal, said local step indicating a maximum, or an abrupt or sudden change in a parameter calculated based on a predetermined interval of the of the segment score signal values, e.g. the mean level of a predetermined interval of the of the segment score signal values. The processor may combine the local step and the global step to obtain a combined step, and may determine a transition in the image stream from one anatomical segment to another, such that the point of transition correlates to the combined step.

In some embodiments, the processor may calculate a feature vector for each selected image, the feature vector based on: a villi score (which may correspond to an amount of villi texture or structures found in a selected image), a content score (which may correspond to a probability that a selected image depicts intestinal contents) and/or a white score, the white score corresponding to pixels in a selected image which are substantially white).

The processor may be configured to detect a bubble sequence in the image stream, the bubble sequence corresponding to a sequence of images, wherein each image of the sequence contains at least a certain predetermined amount of bubbles. The processor may correct the point of transition according to the detected bubble sequence. The processor may detect a low segment score sequence (corresponding to a sequence of image frames which received a low segment score), and may detect an intersection or overlap of the bubble sequence and the low segment score sequence. Based on the intersection or overlap, the processor may determine the middle of the bubble sequence as a corrected point of transition in the image stream, or may determine the corrected point of transition as a next step detected in the segment score signal.

The processor may determine a noisiness level of the segment score signal. If the noisiness level of the segment score signal is above a predetermined threshold, the processor may calculate a tissue area score for each selected image to obtain a tissue area score signal, the tissue area score per image indicating an amount of tissue which is captured in an image, determine a step in the tissue area score signal, and determine a point of transition in the image stream according to the detected step in the tissue area score signal. The processor may refine the detected point of transition of the image stream by selecting a new subset of images from the image stream, the new subset selected from the vicinity of the detected point of transition, and computing a refined point of transition using the new subset of images.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The principles and operation of the system and method according to the present invention may be better understood with reference to the drawings, and the following description, it being understood that these drawings are given for illustrative purposes only and are not meant to be limiting, wherein:

FIG. 1 shows a schematic diagram of an in-vivo imaging system according to an embodiment of the present invention;

FIG. 11 is a flow chart of a method for determining a step in a segment scores function according to an embodiment of the invention;

FIGS. 14A and 14B depict graphs of segment score functions according to an embodiment of the invention;

FIG. 15 illustrates phases of bubble detection according to an embodiment of the invention;

FIG. 16A is a flow chart of a method for determining a transition point in an image stream which includes at least one bubble sequence according to an embodiment of the invention;

FIG. 17 is a flow chart of a method of determining a transition point in an image stream according to an embodiment of the invention;

FIG. 18A is a flow chart of a method for determining noisiness of a segment score signal according to an embodiment of the invention;

FIG. 18B depicts graphs of a segment score signal and its corresponding a local edge signal according to embodiments of the invention.

Figure 2A:
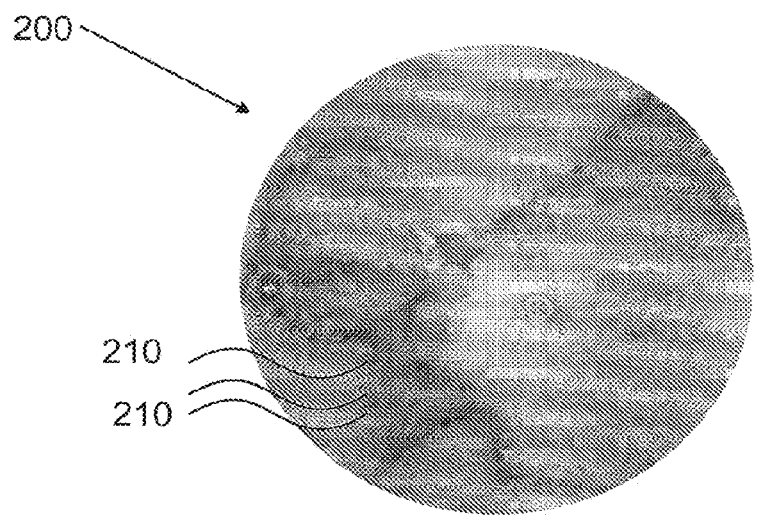
FIG. 2A is an exemplary small bowel image depicting villi structures according to an embodiment of the present invention.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

DETAILED DESCRIPTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Some embodiments of the present invention are directed to a swallowable in-vivo device, such as an autonomous swallowable capsule. Other embodiments need not be swallowable or autonomous, and may have other shapes or configurations. Devices according to embodiments of the present invention, including imaging, receiving, processing, storage and/or display units suitable for use with embodiments of the present invention, may be similar to embodiments described in US Patent Application Publication Number 2006/0074275, entitled "SYSTEM AND METHOD FOR EDITING AN IMAGE STREAM CAPTURED IN-VIVO", U.S. Pat. No. 5,604,531 to Iddan et al., entitled "In-vivo Video Camera System", and/or in U.S. Pat. No. 7,009,634 to Iddan et al., entitled "Device for In-Vivo Imaging", each assigned to the common assignee of the present application. Of course, devices and systems as described herein may have other configurations and other sets of components. Devices, systems and methods according to some embodiments of the present invention may be similar to the commercial PillCam® SB2 or PillCam® Colon capsules and the associated data recorders and RAPID® workstation provided by Given Imaging, Ltd.

Reference is made to FIG. 1, which schematically illustrates an in-vivo imaging system according to an embodiment of the invention. According to some embodiments, the system may include a device, for example, a capsule 40. Capsule 40 may be a swallowable in-vivo capsule, but other sorts of devices or suitable implementations may be used. According to one embodiment, capsule 40 may communicate with an external receiving and display system to provide display of data, control, or other functions. For example, power may be provided by an internal battery 41 or a wireless energy receiving system. Other embodiments may have other configurations and capabilities.

Capsule 40 may include one or more imagers 46 for capturing images, one or more illumination sources 42 for illuminating the body lumen, and a transmitter 45 for transmitting image data and possibly other information to a receiving device such as receiver 12. Transmitter 45 may include receiver capability, for example, to receive control information. In some embodiments, the receiver capcbility may be included in a separate component. An optical system, including, for example, lenses 49, lensholders 44 or mirrors, may aid in focusing reflected light onto the imagers 46. The lensholders 44, illumination units 42, and imagers 46 may be mounted on a substrate 56. An imaging head 57 and/or 58 may include the optical system, optical dome 54, imager 46, illumination units 42, and substrate 56.

Preferably, located outside the patient's body in one or more locations, are an image receiver 12, preferably including an antenna or antenna array, an image receiver storage unit 16, one or more data processors 14, 15, a data processor storage unit 19, and an image monitor 18, for displaying, for example, the images recorded by the capsule 40. Preferably, the image receiver 12, data processor 14 and image receiver storage unit 16 are small and portable, and are worn on the patient's body during recording of the images. The data processor 15, data processor storage unit 19, and image monitor 18 may be included in a computer or workstation 11, or may be included in the image receiver. Data processors 14 and/or 15 may be configured to carry out all or part of methods according to the present invention by for example executing software or code, and/or including dedicated modules or processors.

According to embodiments of the present invention, data processor 14 may receive images and telemetry data received by image receiver 12, for example in real time, or with a minimal delay. According to an embodiment of the invention, the data processor 14 may include an anatomical region detector 13 for determining an anatomical region in which an image was captured. Anatomical region detector 13 may be an anatomical region processor and may be implemented by data processor 14. While the anatomical region detector 13 is shown in FIG. 1 as being separate from and connected to processor 14, in some embodiments anatomical region detector and other modules and detectors described herein may be a set of code or instructions executed by, for example, processor 14 (or another processor such as processor 15). Anatomical region detector 13 may be or may include one or more dedicated processors. The anatomical region detector 13 may evaluate the degree or occurrence in each frame of qualities based on each of a plurality of pre-defined criteria defined, for example, in, by or for, the anatomical region detector 13 or in a separate storage unit. For example, the anatomical region detector 13 may process the images and/or the telemetry data, and determine, for example in real time, whether images, or portions thereof, are/were captured in the gastric region, in the small bowel region of the gastrointestinal tract, or in a different region (e.g. the colon). In some embodiments, a series of operations and pre-defined criteria and rules may be used to determine the anatomical region in which the image was captured. For example, anatomical region detector 13 may determine whether an image includes villi structures or patterns, which are structures/patterns typically found in the small bowel. If villi structures or patterns are detected in one or more images from an image stream, the anatomical region detector 13 may determine that the capsule has transited to the small bowel. If no villi structures are detected, or if a small amount of villi structures are detected in an image stream or a portion thereof (e.g., compared to a threshold amount), for example over a predetermined period of time of image capturing, or over a predetermined number of consecutive images, anatomical region detector 13 may determine that the capsule is capturing images in the stomach, or that the capsule has passed on to the colon. A threshold for determining whether a sufficient amount of villi structures is present in an image stream or a portion thereof may be determined, for example, empirically. For example, a threshold condition for deciding that no villi were detected (or an insufficient amount of vili structures were detected), may be that the sequence of images in which no villi were detected is sufficiently long, e.g. a sequence of over one or two hours of captured images, or a sequence of over 50,000 images.

A score, rating, or measure may be calculated by anatomical region detector 13 for example for each image that is received by image receiver 12, or for selected images. For example, in some embodiments, images for processing by anatomical region detector 13 may be selected from a number of consecutive images (e.g., only every 5th image may be processed) or from a set of images received within a predetermined time period (e.g. 1 minute). In some embodiments, the anatomical region detector 13 may generate a simplified representation (e.g., a derived value or rating, such as an integer 0-100) of more complex characteristics of an image or a portion of an image (e.g., criteria, such as, color variation, appearance of certain textural or structural patterns, light intensity of the image or portions thereof, etc.). A score may include or embody any rating, rank, hierarchy, scale or relative value(s) of features or criteria. Typically a score is a numerical value, for example, a number from 1 to 10, but need not be limited as such. For example, scores may include, for example, a letter (e.g., A, B, C, . . . ), signs or symbols (e.g., +, −), computer bit values (0, 1), the results of one or more decisions or conditions (e.g., yes no), for example, indicated by the status of one or more computing flags. Scores may be discrete (non-continuous) values, for example, integers, a, b, c, etc., or may be continuous, for example, having any real value between 0 and 1 (subject to the precision of computer representation of numbers). Any interval between consecutive scores may be set (e.g., 0.1, 0.2, . . . , or 1, 2, . . . , etc.), and scores may or may not be normalized.

Scores for each frame, or for one or more portions thereof, may be stored, for example associatively, with the frame in the same database (e.g., image receiver storage unit 16). The scores may be defined, e.g., in a header or summary frame information package, for example with the data in an initial image stream. Alternatively or additionally, the scores may be stored in a database separate from the images, with pointers respectively pointing to the images.

In one embodiment, anatomical region detector 13 may assign a single combined score, e.g., a scalar value rating each frame or group of frames based on predetermined criteria or operations, for example as described in connection with FIG. 5. A score calculated for an image may indicate whether the image is a small bowel image or a stomach (gastric) image. For example, a value of '0' (zero) may be assigned to images which are suspected to be stomach images, while a value of '1' (one) may be assigned to images which are suspected to be small bowel images. In another embodiment, anatomical region detector 13 may assign a probability value to the image, for example a value of '53' may indicate that the detector calculated 53% probability that the image was captured in a certain (e.g. predetermined) segment of the GI tract, e.g. in the small bowel. Other values may be assigned, and other regions may be determined by anatomical region detector 13.

The scores or measures may be absolute or relative to each other, and may be calculated, for example, based on a sequence of frames or on a single frame. The absolute score(s) for each frame or portion of frame may be a value associated with the criteria for the single frame. The relative score(s) for each frame or for a portion of frame may be a change in the value associated with the criteria relative to the value associated with the criteria for a previous or adjacent frame. Both absolute and relative scores may or may not be scaled (normalized). Scores may be scaled using a different scaling factor, for example, for images captured using different frame capture rates.

The original image stream may be divided into portions or segments. A portion or segment may be defined according to the GI tract organ or GI tract anatomical segment. For example, a first segment of the image stream may include all images of the stream captured in the esophagus, a second segment may include all images of the stream captured in the stomach, a third segment may include all images of the stream captured in the small bowel, and a fourth segment may include all images of the stream captured in the colon. Additionally, sub-segments may be defined and detected in the stream, and these as well may be referred to as anatomical segments. For example, the colon may be segmented to the ascending colon, the transverse colon, and the descending colon. The small bowel may be segmented to, for example, the duodenum, the jejunum, and the ileum. The segmentation may be performed based on, for example, classification of images to a small bowel segment or a gastric segment by anatomical region detector 13.

According to one embodiment, anatomical region detector 13 may process images or portions of images from one or more image streams captured by one or more imagers 46. For example, a double-headed capsule 40 may capture two image streams using two separate optical systems. The received image streams may be processed separately. For example, each stream may be processed as a separate stream, and for each image anatomical region detector 13 may determine independently in which anatomical region the image was captured. In other embodiments, streams may be merged, for example images from two or more streams may be sorted chronologically according to the capture time of the images, and merged into (e.g., to create) a single stream, then processed as a single image stream. Other sorting methods are possible, for example based on different image parameters such as similarity between images, or based on other scores assigned to the images by different filters, or detectors (e.g. pathology or abnormality detectors). The merged stream may be processed as one stream (e.g., anatomical region detector 13 may sequentially process images from the merged stream instead of separately from each stream). In some embodiments, images may be processed simultaneously, for example using more than one processor in parallel processing. In yet another example, each stream may be processed separately, and anatomical region detector 13 may determine an anatomical region for images of each stream, or points of transition between anatomical regions for each stream. Additionally, anatomical region detector 13 may verify that the points of transition, or transition points, between anatomical regions are detected in the separate image streams, thus reducing possible errors in detection of the transition points if the detection occurs only in one image stream.

According to one embodiment of the invention, data processor 15, data processor storage unit 19 and monitor 18 may be part of a personal computer or workstation 11 which includes standard components such as a processor, a memory, a disk drive, and input-output devices, although alternate configurations are possible, and embodiments of the system and method of the present invention may be implemented on various suitable computing systems. An input device 24 may receive input from a user (e.g., via a pointing device, click-wheel or mouse, keys, touch screen, recorder/microphone, other input components) and send corresponding commands to trigger control of the computer components, e.g., data processor 15.

Data processors 14 and 15 may be configured to carry out methods as disclosed herein, for example by executing software or code stored in memories. Data processors 14 and 15 may include one or more standard data processors, such as a microprocessor, multiprocessor, accelerator board, or any other serial or parallel high performance data processor. Image monitor 18 may be a computer screen, a conventional video display, or any other device capable of providing image or other data. In some embodiments, an image and/or text display 51 may be provided in image receiver 12, in addition to or instead of image monitor 18.

Preferably, the imager 46 is a suitable ccomplementary metal-oxide-semiconductor (CMOS) camera, such as a "camera on a chip" type CMOS imager specified by Given Imaging Ltd. of Israel and designed by Photobit Corporation of California, USA. In alternate embodiments, the imager 46 may be another device, for example, a charge-coupled device (CCD). The illumination source 42 may be, for example, one or more light emitting diodes, or another suitable light source.

During an in vivo imaging procedure, imager 46 may capture images and send data representing the images to transmitter 45, which transmits images to image receiver 12 using, for example, electromagnetic radio waves. Image receiver 12 may transfer the image data to image receiver storage unit 16. In some embodiments, image data stored in storage unit 16 may be sent and processed immediately, e.g. in real time or substantially in real time, in the data processor 14. In other embodiments, after a certain period of time of data collection, the image data stored in storage unit 16 may be sent to the data processor 15 or the data processor storage unit 19. For example, the image receiver storage unit 16 may be taken off the patient's body and connected to the personal computer or workstation which includes the data processor 15 and data processor storage unit 19 via a standard data link, e.g., a serial or parallel interface of known construction.

Data processor 14 may analyze the data, for example, by activating anatomical region detector 13, and may store the result, for example per image. In some embodiments, the result may be provided to a user in real time, for example an indication or notification that the capsule 40 has passed from the stomach to the small bowel may be provided to the user. In one embodiment, a notification unit 25 may activate a sound alert, illuminate an LED 50, and/or display a message on an image monitor/screen 51 which may be operationally connected to data processor 14 or to image receiver 12. Such indication may be useful for a patient during an imaging procedure, for example an indication of the capsule's transit into the small bowel may induce, or prompt, the patient to take a certain medication or perform another operation related to the medical procedure. The notification may indicate, for example, that the imaging device has entered a specific organ or transited into a specific region of the gastrointestinal tract (e.g., the small bowel), or that the imaging device entered the organ at or near the time the relevant image was captured. In some embodiments, the notification may be made in real time to a user, while other embodiments allow indication at a later time, for example an indication may be provided to a user reviewing the image stream after the procedure has been completed that the capsule transited into a certain region or organ.

Data processor 14 may execute or operate software or code (e.g., stored in storage 16) which, in conjunction with basic operating software such as an operating system and device drivers, controls the operation of data processor 14. According to one embodiment, the software controlling data processor 14 may include code written, for example, in the C++ language and possibly alternative or additional languages, and may be implemented in a variety of known methods.

The image data collected and stored may be stored indefinitely, transferred to other locations, manipulated or analyzed. A health professional may use the images to diagnose pathological conditions of, for example, the GI tract, and, in addition, the system may provide information about the location of these pathologies. While using a system where the data processor storage unit 19 first collects data and then transfers data to the data processor 15, the image data is not viewed in real time. When using a system in which data processor 14 receives the data by data receiver 12 and processes or partially processes immediately (e.g., substantially upon image receipt, the image may be processed), real time or quasi-real time viewing is possible.

According to one embodiment, the capsule 40 may collect a series of still images as it traverses the GI tract. The images may be later presented as, for example, a stream of images or a moving image of the traverse of the GI tract. One or more in-vivo imager systems may collect a large volume of data, as the capsule 40 may take several hours to traverse the GI tract. The imager(s) 46 may record images at a rate of, for example, two to forty images per second each (other rates, such as four frames per minute, may be used). The imager(s) 46 may have a fixed or variable frame capture and/or transmission rate. When the imager(s) 46 have (e.g., are configured to operate using) a variable or adaptive frame rate (AFR), the imager(s) 46 may switch back and forth between frame rates, for example, based on parameters, such as the capsule 40 speed, its estimated location, similarity between consecutive images, or other criteria. Thousands of images, for example over 300,000 images, may be recorded. The image recordation rate, the frame capture rate, the total number of images captured, the total number of images selected for the edited moving image, and the view time of the edited moving image, may each be constant or variable.

Preferably, the image data recorded and transmitted by the capsule 40 is digital color image data, although in other embodiments other image formats may be used. In an exemplary embodiment, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by a one byte (i.e., 0-255) brightness value. According to one embodiment, images may be stored sequentially in data processor storage unit 19 and/or in image receiver storage unit 16. The stored data may include one or more pixel properties, including color and brightness.

While, preferably, information gathering, storage and processing are performed by certain units, the system and method of the present invention may be practiced with alternate configurations. For example, the components gathering image information need not be contained in a capsule, but may be contained in any other vehicle suitable for traversing a lumen in a human body, such as an endoscope, stent, catheter, needle, etc.

Data processor storage unit 19 may store a series of images recorded by a capsule 40. The images the capsule 40 records as it moves through a patient's GI tract may be combined consecutively to form a moving image stream or movie.

Figure 2B:
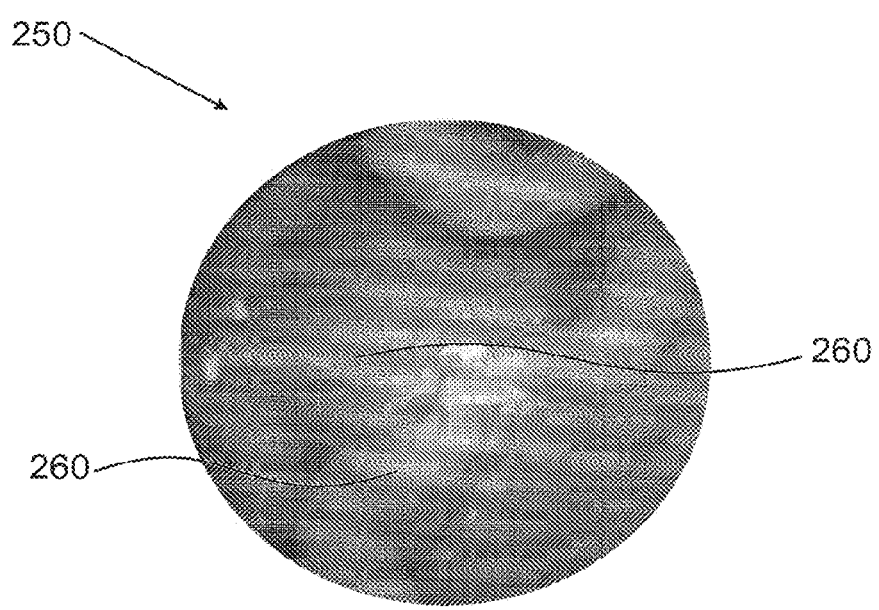
FIG. 2B is an exemplary gastric region image according to an embodiment of the present invention.

Reference is now made to FIGS. 2A and 2B, which depict an exemplary in vivo image 200 of the small bowel (2A) and an exemplary in vivo image 250 of the gastric region (2B). Image 200 includes numerous villi patterns 210, which are repeated hair-like structures/patterns, typically protruding from the mucosa of the small bowel. Detecting villi structures/patterns may indicate that images captured by the imaging device were captured in the small bowel. If no villi structures are detected in a series of consecutive images, or if only a small amount of villi structures is detected (e.g., smaller than a predetermined threshold amount), several different scenarios are possible. For example, the imaging device may have captured these images in a different organ or segment of the body lumen (e.g. not in the small bowel), for example in the stomach or the colon, where no villi are typically found. In another example, the images may have been captured in the small bowel, but due to blurring, turbid media and/or content, which may be present in the small bowel, the villi structures may be obscured or undetectable in the images. In yet another example, villi structures may not be present even if the image was captured in the small bowel, for example due to the patient having a certain medical condition such as Celiac or Crohn's disease. These, and possibly other, diseases may damage the villi structures and cause them to disappear to some degree, e.g. partially, substantially or completely. In some embodiments, if no villi pattern is detected in any of the images captured during the whole imaging procedure, or if a small number of images containing villi pattern are detected throughout the imaging procedure or a portion thereof, an indication may be provided to the user, advising her/him of an increased probability of these related medical, or pathological, conditions. In another example, the amount of patches indicated as containing villi in an image may be less than a predetermined threshold amount. In one embodiment, a text message may be displayed, for example on display 51, indicating that no villi pattern has been detected, or that an insufficient amount of villi patterns has been detected, or indicating that Celiac or Crohn's disease is suspected and should be further investigated. In some embodiments, the amount of villi patterns detected may be presented to a user, for example displayed along a normal range or amount of villi patterns or patches including villi patterns in images which are expected to be found in the small bowel. Other alerts and display options are possible.

Image 250 shows an exemplary gastric image, which does not include villi structures/patterns. The tissue walls 260 are substantially smooth, with no visible villi structures.

In some embodiments, detecting images that contain villi patterns may indicate that the imaging capsule has advanced from the stomach to the small bowel. Similarly, if no villi patterns are detected in images after villi patterns have already been detected over a sequence of images, it may be deduced that the capsule has exited the small bowel and continued to the colon. For example, a text message may be displayed on display 51, indicating that the capsule has exited the small bowel.

Figure 3:
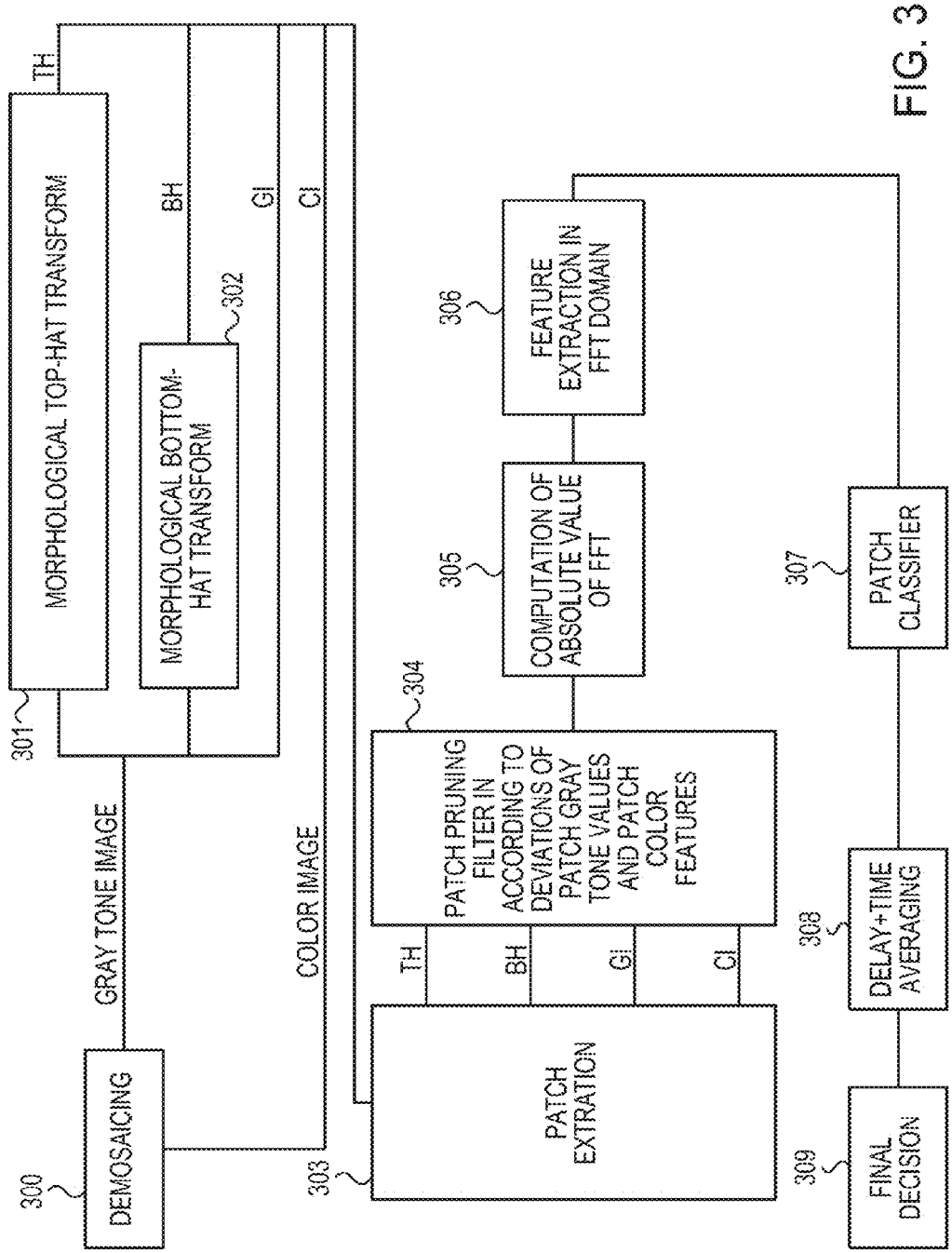
FIG. 3 is a block diagram of a method of detecting villi texture based on image processing in real time according to an embodiment of the present invention.

Reference is now made to FIG. 3, which depicts a flowchart of an algorithm for detecting a specific pattern in an image, e.g. a villi pattern. In operation 300, an image is received from the in vivo device. The image format may be, for example, in raw Bayer mosaic data format. The image may be processed by performing de-mosaicing, and a color image may be generated, for example of 256×256 pixels. Other processing operations are possible, for example the image may be decompressed and/or descrambled before demosaicing. In addition, a gray tone image may be generated from the raw Bayer mosaic data. The image data may have other formats. The generated color images may have other sizes, for example 128×128 pixels, which may be generated, for example, by selecting one out of every 4 pixels. Generating a smaller-sized image may have an advantage of shorter processing time, in some embodiments without a substantial change to the sensitivity and specificity of the result.

Operations 301 and 302 include a pre-processing stage of the grayscale image. The pre-processing may include for example morphological white top-hat transforms 301 and/or black top-hat transforms 302 (also named "bottom hat" transforms). Other or no pre-processing may be used. The white top-hat and black top-hat transforms are used to extract small elements or details from the input images and to emphasize them, while the background and large elements are removed from the image. For example, $f:E \mapsto R$ is a grayscale image, mapping points from a Euclidean space or discrete grid E (such as R2 or Z2) into the Real numbers space. The white Top-hat transform of f is given by: $T(f)=f-f \circ b$, where $\circ$ denotes the opening transform, and b(x) may be a grayscale or a flat structuring element. The details that may be extracted by the top-hat transforms can be controlled by the size of the structuring element b(x). Similarly, the black Top-hat transform (sometimes called a bottom-hat transform), is defined as the residual of a closing compared to the original signal $B(f)=f \bullet b-f$, where $\bullet$ denotes the closing operation. In some embodiments, only a white top-hat transform or only a black top-hat transform may be used in the preprocessing stage.

In one embodiment, a mask of 5×5 pixels may be used as a flat structuring element, which is typically processed faster than a grayscale structuring element. Different sizes of masks may be selected. However, the size of a typical feature in the pattern being sought may determine the minimal size of the mask. For example, a 5×5 pixel mask may be large enough to include a single villus structure, substantially without cropping it. Using this structuring element may allow the transform to keep details that are similarly sized in the image, while removing larger structures which may be irrelevant to the sought pattern. Other mask sizes may be selected, e.g. 7×7.

The output from the morphological preprocessing stage transforms provides the input for operation 303, which includes dividing the image into a plurality of patches of size M×N pixels for further processing. The patches may be partially overlapping, which may cause longer processing time but may be more reliable than selecting non-overlapping patches. The typical size of the sought texture pattern in an image may determine the selected size of the patch. In one embodiment, patches of for example 32×32 or 64×64 pixels may be extracted from the image without overlapping between patches. The patches may be filtered out or pruned in or during operation 304 according to selected characteristics or features of the patch grayscale and color values. In the pruning process, some of the patches may pass on (e.g., continue) to the next stage, while some may be filtered out. The set of filtered patches is typically a subset of the plurality of patches extracted for an image. For example, for each patch, one or more of the following parameters may be calculated: average R value of the patch (where R denotes the red pixels value of the RGB image), average G (green) value, average B (blue) value, average(G)/average(R), and average (B)/average(R). In another example, the pruning process may be based on a logarithm of the color or the gray level images, to compensate for differences in lighting conditions. In addition, the deviation of the gray-scale values in the image may be calculated, for example by calculating the mean of the absolute change between each pixel's values to the average value of the patch. Each parameter may have a threshold condition which may be determined, for example empirically, based on a database of input image streams. Any learning algorithm may be used to determine the threshold conditions, for example a histogram of each parameter may be generated, and the range of values selected as the threshold condition may be determined by selecting a bottom value such that 99.5% of the values are above it, and a top value such that 99.5% of all values are below it. Based on the threshold of the parameters, it may be determined whether the patch is qualified to continue to the next operation or not. Each patch that does not pass the threshold conditions of operation 304 may be assigned a value of 'zero' in operation 304 (e.g., no villi texture was detected in this patch). Other values or scores may be assigned to indicate that the patch does not include detected villi structures.

Figure 4:
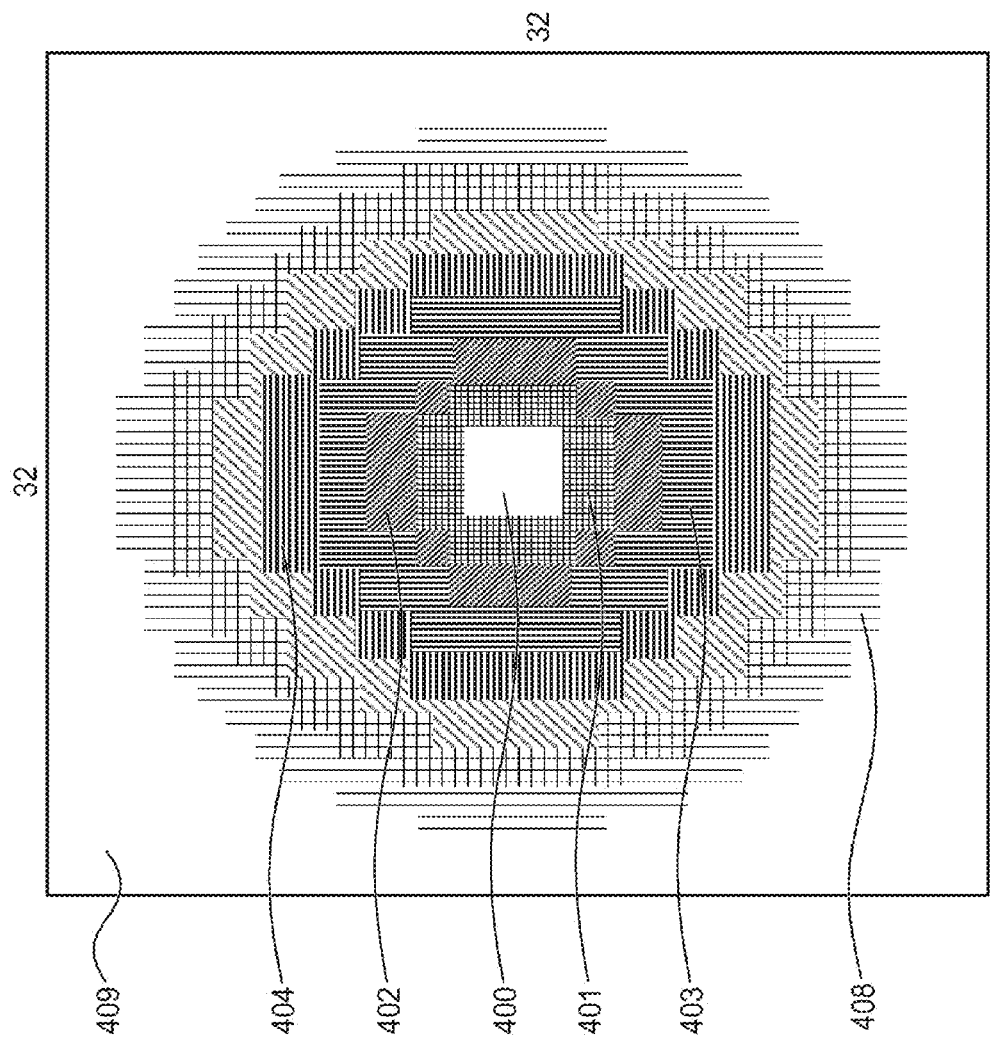
FIG. 4 is an exemplary ring filter according to an embodiment of the invention.

In operation 305, Fast Fourier Transform (FFT) is performed on each patch that passed the threshold condition. The result may be used to extract rotation-invariant textural features (operation 306) by means of, for example, ring filters. For example, a maximum function may be applied to the FFT values along a number of rings or ring-like shapes, for example as shown in FIG. 4. The rings, e.g. rings 402, 403, 404 and 408, may be selected to cover substantially all pixels of the patch in the Fourier domain. In some cases, some ring features may be disregarded or ignored, due to their low discrimination ability. For example, excluding the highest frequency ring 409 and lowest frequency ring 401, along with the central DC point 400 in a patch of 32×32 pixels in the Fourier domain, may result in a predetermined number, e.g. 12, of rotation-invariant ring features. Other features may be selected and calculated, in addition to or instead of the ring features.

The features extracted from the FFT domain may provide the input to a classifier in operation 307. The classifier may determine whether the patch includes the sought villi pattern or not. Some of the patches that passed the threshold condition will be assigned the value 'one' by the classifier in operation 307, indicating that villi texture has been detected in these patches, and others may be assigned the value 'zero'. The values per patch may be stored, for example in a storage unit in image receiver 12 or in a different storage unit. In one embodiment, the number of patches from the whole image that are assigned the value 'one' may be counted (e.g., the number of patches in each image identified as including villi structure), and the total count may be stored per image, for example in image receiver storage unit 16.

In operation 308 a delay and averaging operation may be performed. For each selected or analyzed image, a score may be calculated by averaging, over a sequence of images, the total count of number of patches that received a value 'one'. In some embodiments, the calculation may be performed for a predetermined number of sequential images before the current image (e.g. 10 or 25) and/or a predetermined number of images after it (e.g. 10 or 25). In this case, the calculation of the average score may be delayed until the images captured after the current image are received and processed, for example by anatomical region detector 13. In some embodiments, the calculation may be performed only on the predetermined number of previous images, e.g. 50, for example when using a single imaging system. When using, for example, a double-headed capsule (e.g. a capsule with two imaging systems) for an imaging procedure, 25 previous images captured by each head may be used. Other numbers of images may be used for the averaging operation, for example the number may depend on the frame capture rate of the capsule, and/or on the amount of time that passed since the start of the imaging procedure, or other considerations/parameters.

In operation 309, based on the score calculated in operation 308, a final decision may be determined based on one or more threshold conditions. If the average number of patches determined to include villi texture in a set of consecutive images (e.g., neighboring or near the current image) is high enough, for example above a predetermined threshold, the current image may be determined to be a small bowel image. Otherwise, the current image may be determined to be a stomach image. In some embodiments, a score combining a sequence of images need not be calculated, and the final decision may be determined based on whether the number of patches in a single image passed a threshold condition (for example, if villi pattern was detected in four or more patches of an image, the image may be determined to be a small bowel image). According to some embodiments, once a small bowel image has been detected, the algorithm may stop its operation (e.g., due to a physiological presumption that once the imaging capsule has advanced from the stomach to the small bowel, it will not go back again but rather continue to advance forward towards the colon). In other embodiments, the villi detection process may continue while the capsule is traversing the small bowel. In the colon there are typically no villi structures, therefore a transition from the small bowel to the colon may be determined based on detecting that no more villi structures are present in the images, for example in images captured after the small bowel has been detected.

Figure 5:
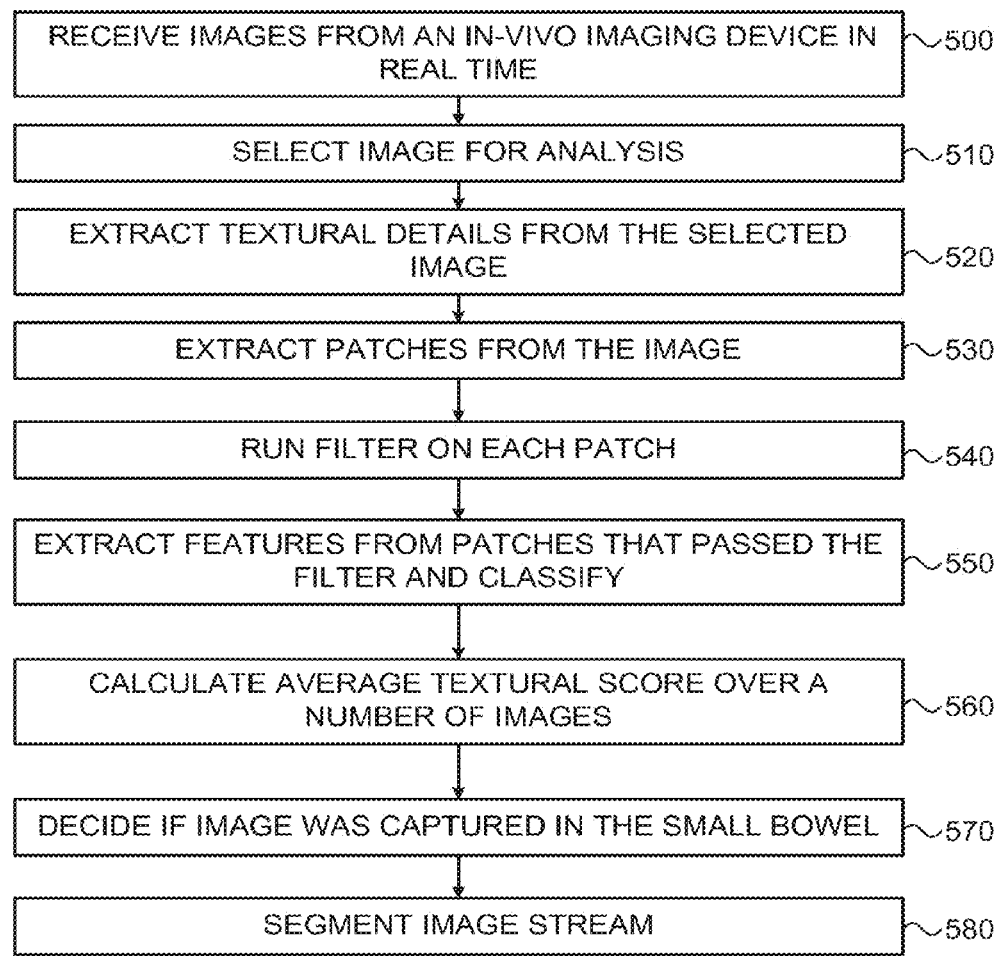
FIG. 5 is a flowchart of a method for segmenting an image stream according to an embodiment of the present invention.

Reference is now made to FIG. 5, which depicts a flowchart of a method according to an embodiment of the present invention. In operation 500, images sent from an in vivo imaging device may be received, for example by an image receiver 12. The images may be received in real time (e.g., as soon as an image is captured, it is transmitted and received), substantially in real time, or with an introduced delay. The images may be captured and sent in different frame rates, for example the capsule may change its frame rate from time to time, and in some time periods two images (for example) per second may be received, while in other time periods 40 images (for example) per second may be received. In operation 510, one or more images for analysis of villi structures may be selected from the received image stream. In some embodiments, each image received may be analyzed. Other embodiments may allow a subset of images to be analyzed, for example by selecting one image for analysis in every predetermined time period (e.g. one image every second), or one image in every predetermined number of images (e.g. one out of 10 received images). Image selection may also vary according to the frame capture rate of the capsule 40, or according to other parameters of the video stream, or as desired. In some embodiments, images may be received from more than one imager simultaneously, e.g., in a double headed imaging capsule 40, images may be received from a first imaging system and a second imaging system. The selection of images in this case may be such that images are selected from both imaging systems, or from a single imaging system.

In operation 520, a selected image may be processed to remove background and enhance certain textural details in the image. For example, a top-hat transform may be applied to the image, using a specific mask which will enhance small villi structures in the image, while substantially removing larger structures which may be present in the image. After the texture processing, patches may be extracted from the result image (operation 530). The size of the patches may be a predetermined constant, and may be dependent on the image resolution/size, and/or on the sought texture. The image may be divided into L patches of size M×N pixels for further processing. For example, an image of size 256×256 pixels may be divided into 64 patches of size 32×32 pixels each. Other image sizes and resolutions may be used in a similar manner. In some embodiments, patches may be extracted such that each patch partially overlaps other patches to a certain degree, for example patches may have 30% or 50% overlap with neighboring patches.

In operation 540, a filter or pruning process may be applied to each patch. The filter may include a set of threshold conditions which may be checked for each patch. In some embodiments, only patches that pass some or all of the threshold conditions may continue to a next stage of processing. Threshold conditions may be calculated, for example, based on the statistics of the grayscale or color features extracted from patches. Examples of threshold conditions include, but are not limited to, average R value of the patch (where R denotes the red pixels value of the RGB image), average G value, average B value, average(G)/average(R), and average (B)/average(R).

In operation 550, features may be extracted from patches that passed the filter, for example ring features in the Fourier domain as described in operation 306 of FIG. 3. A classifier may receive the extracted features, and determine for each patch whether villi structures are present in it. The result may be stored per patch, for example a simple score may be assigned by the classifier to each patch, e.g. a score of "zero" indicating no villi structures were identified, or a score of "one" indicating presence of villi structures in the patch. A total count of the number of patches per image that received a positive villi indication may be calculated and stored as a Sum score per image. Other methods of determining a summary score for an image based on patches to determine a final image score or rating may be used.

In operation 560, the Sum score may be used to calculate an average score which will be used as a final score or rating of the image. In one embodiment, the score may be averaged based on Sum scores of the current image and its neighboring images. The final score may be, for example, an average of the Sum scores per image, averaged over a predetermined number of consecutive or adjacent images For example, the final score may be calculated by averaging the Sum scores of the current image and 49 previous images. Thus the final score for current image X may be an average of the Sum score of the current image X and the Sum scores of a predetermined number of previous and/or next images.

In some embodiments, the set of images averaged for the calculation of the averaged final score of a current image may include previous images and/or successive images. In this embodiment, the calculation of the averaged final score may be delayed until the Sum scores are calculated for the subsequent images.

In some embodiments, the images used for the calculation are only images which have been selected for analysis in operation 510. Therefore, in embodiments in which not every image is analyzed, a set of "consecutive" images may include images which are not immediately sequential in the original image stream received from the capsule 40. The images may be consecutive or adjacent images, or neighboring images in the originally captured image stream, but in some cases there may be gaps between the images being averaged, for example if not all images from the original image stream are selected to be analyzed or processed for villi detection.

In operation 570, it is determined whether an image includes the villi structure or not. This decision may be determined based on a threshold condition for the final score calculated in operation 560. If the set of consecutive or sequential images include a sufficient average amount of patches with villi texture, then it may be determined that the image is a small bowel image. In some embodiments, if the final score passes a predetermined threshold, an indication of an anatomical transition of the imaging device may be provided, either in real time during the image capturing procedure, or at a later time for example when reviewing the image stream. The transition may include, for example, passage of the capsule 40 from the stomach region to the small bowel, or passage of the capsule 40 from the small bowel to the colon.

According to some embodiments, once a decision is taken that an image is a small bowel image, the analysis process may quit, since physiologically, it is unlikely that a capsule that passed into the small bowel will go back to the stomach or gastric region. In some embodiments, the analysis process may continue in the small bowel. For example, upon detecting that a predetermined number of consecutive images do not include the villi pattern, it may be determined that the capsule 40 has passed from the small bowel into the colon. The gastric, small bowel and colon regions may be segmented in this method (operation 580), e.g. a first image or sequence of images containing a sufficient amount of villi structures may indicate the entrance to the small bowel, and a first image or sequence of images indicating no villi structures (after the small bowel was detected) may indicate the entrance to the colon. Segmenting the image stream may include indicating anatomical regions in the image stream, e.g. images corresponding to the stomach, images corresponding to the small bowel and images corresponding to the colon. Landmark points in the GI tract may be determined as part of the segmentation process, each landmark point may indicate the end of one segment and the beginning of another segment or anatomical region. For example, one or more landmark images indicating the cecum may be determined as the end of the small bowel segment and/or the beginning of the colon segment. The GI organ segmentation may additionally include finer segments or sub-segments, for example the duodenum, the jejunum, and the ileum, the ascending colon, the transverse colon, the descending colon, etc. In some embodiments, each image may be classified as belonging to a certain anatomical segment and/or sub-segment, e.g., the esophagus, the stomach, the small bowel, the ascending colon, the transverse colon, the descending colon and/or the rectum. Other anatomical segments may be indicated, and in some embodiments the user may select which anatomical segments he wishes to view or to segment the stream according to. Other segmentation methods of the gastrointestinal tract are possible.

The user may be notified or alerted, for example in real time using notification unit 25 which may be operationally connected to image receiver 12, that the capsule entered the small bowel, the colon, or other anatomical regions. In some embodiments the user need not be alerted in real time, for example the indication of villi detection may be used to segment the image stream to anatomical structures of the gastrointestinal tract at a later time, e.g., when a physician is reviewing the stream. In some embodiments, not all the above mentioned operations are essential and the method may be implemented using a subset of the operations.

Figure 6:
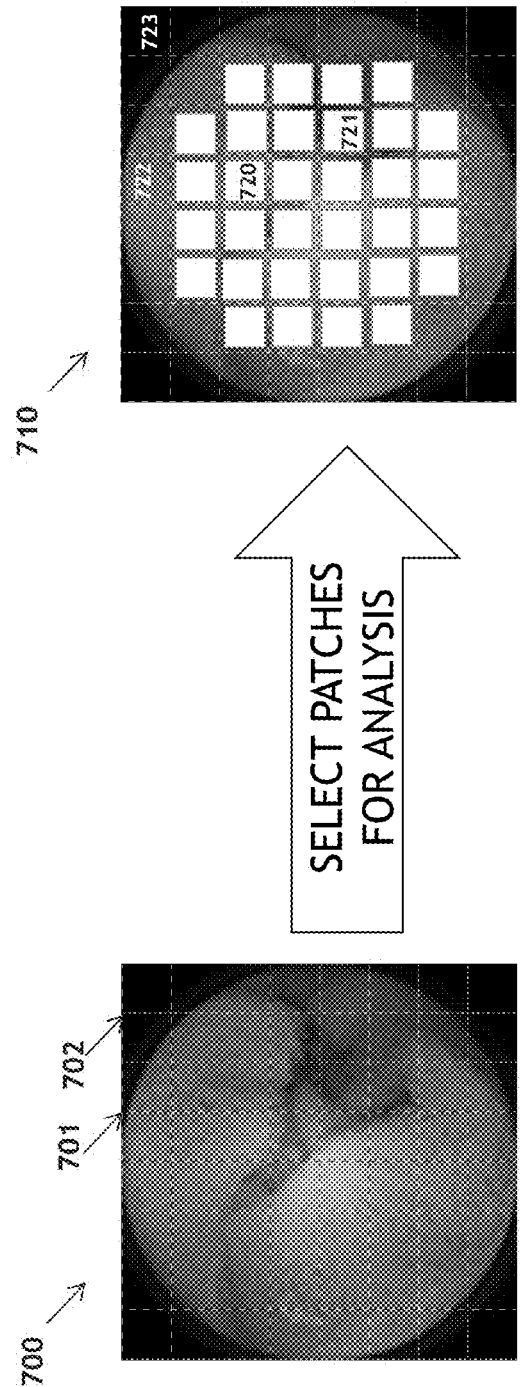
FIG. 6 shows an exemplary division of an image into patches and selection of patches according to an embodiment of the invention.

Reference is now made to FIG. 6, which depicts an exemplary in vivo image or frame 700 which may be divided into portions, segments or patches. For example, image 700 may be divided into 64 equally-sized rectangular patches, as shown by the black dotted line grid (e.g. lines 701, 702), added to image 700. The image 700 may be divided into other numbers of segments or patches, e.g. M by N patches, which may or may not overlap each other (M and N indicate natural numbers).

From the set of patches in image 700, a subset of patches may be selected for transition analysis. A transition in an image may occur, for example, when properties of the imaged scene or view change substantially. In one example, a transition occurs when an imaging capsule transits from the stomach to the small bowel. In another example, a transition occurs when the imaging device passes from the small bowel to the colon. Other transition points may be identified or defined. Examples of transition points may include, but are not limited to, the cecum, the duodenum, the splenic flexure, the hepatic flexure, the Z-line, the rectum, etc. The transition points may include anatomic landmarks which are detected in the image stream.

For example, as shown in image 710, out of the 64 patches, only 32 patches are selected for transition analysis (the selected patches are indicated by a white square e.g. patches 720, 721). The other patches, located in the periphery of the image, such as patches 722 and 723, are not included in the subset of patches which may be analyzed by the processor. Such selection of patches may be driven, for example, by the ROI (Region of Interest), which is the region of the image which includes the meaningful or useful data for image analysis (e.g., not too dark and not too blurred or distorted due to limitations of the imaging devices illumination and/or optical system). In some embodiments, the computations described herein may be performed for the selected patches. However, not necessarily all computations may be performed only for selected patches—some computations may be performed for the whole image according to embodiments of the present invention. In some embodiments, other methods of selecting the patches for analysis may be used.

Differences between tissues imaged in the different organs of the GI tract may include textural properties (e.g. villi texture which may normally be present in the small bowel only) and/or color-related properties, for example the small bowel may usually be more reddish in color, while the colon may be more yellowish in color. These properties may be used, in combination or separately, to detect a transition of the imaging device in the GI tract from one organ to another. Other differences between imaged organs may be used to differentiate between the organs and to detect the transition of the imaging device from one organ to the next. For example, in the colon, typically more intestinal content exists compared to the stomach or the small bowel, due to the nutritional preparation that patients undergo before a medical imaging procedure. The properties may be used as input to a classifier, e.g. a processing unit such as processor 15 or data processor 14 and/or anatomical region detector 13, which may be configured or adapted to perform image processing and to classify images as belonging to a certain segment of the GI tract. Possible segments of the GI may include, but are not limited to, a stomach segment, an esophageal segment, a colon segment, or an SB segment. Other classes (e.g. organs, segments of the GI or sub-segments of the GI) may be used. Images classified as stomach images may include images which were captured in the stomach segment, images classified as small bowel images may include images which were captured in the small bowel segment, etc.

Figure 7:
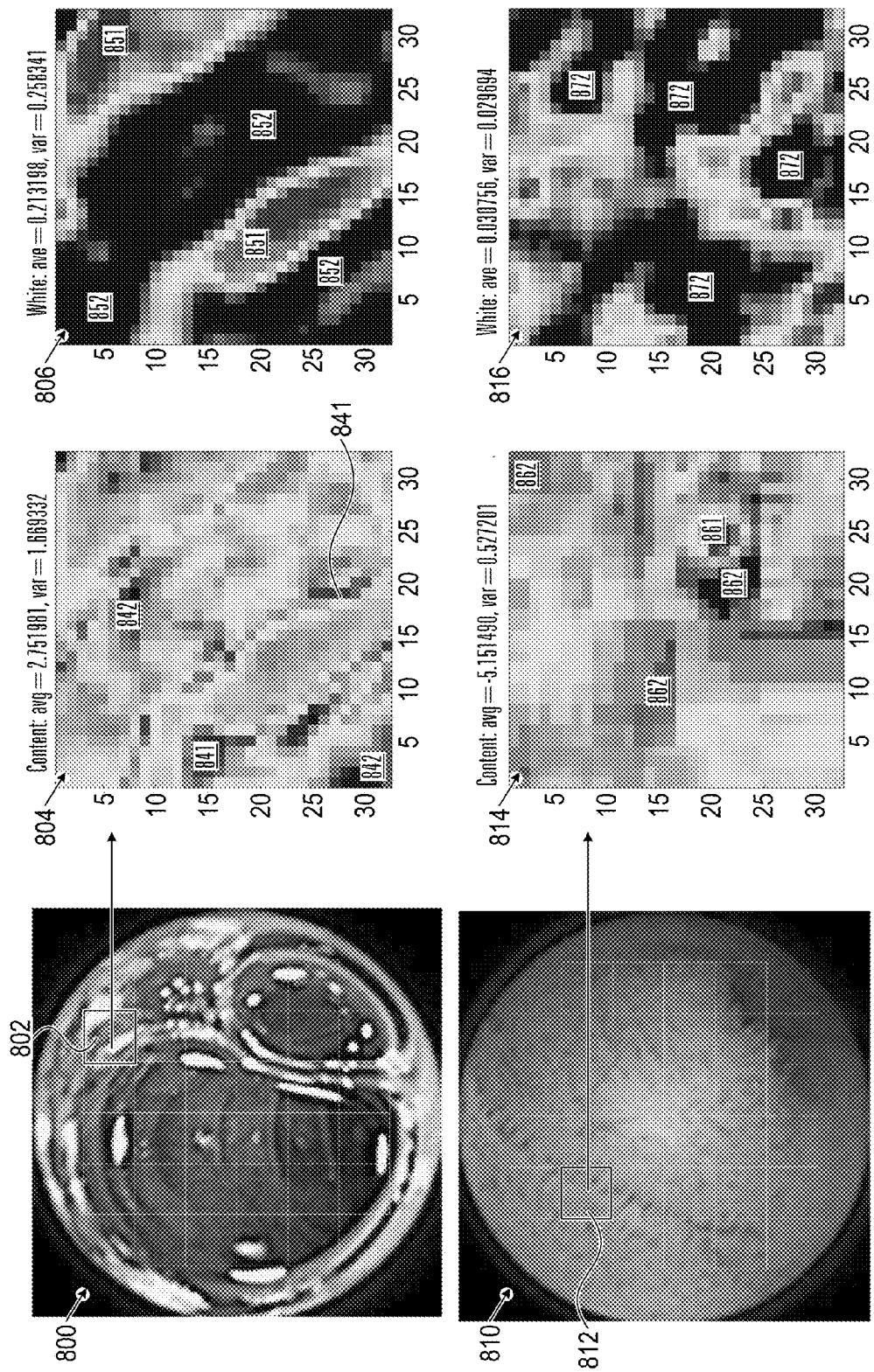
FIG. 7 depicts two images captured by an in vivo imaging device and analyzed according to an embodiment of the invention.

Reference is now made to FIG. 7, which depicts two images 800, 810 captured by an in vivo imaging device. Image 800 was captured in the colon, while image 810 was captured in the small bowel. One or more patches from each image, e.g. patch 802, which is one of the patches selected for analysis in the image 800, or patch 812 selected for analysis from image 810, may be analyzed, for example by computing one or more predetermined scores, features or properties which may be based on pixel values of color, brightness and/or textural features detected in the selected patch.

For example, content score result 804 represents the content score computed per pixel of patch 802. Similarly, content score result 814 represents the content score computed per pixel of patch 812. The content score calculated per pixel is a measure which corresponds to the probability that the pixel depicts intestinal contents (such as turbid contents, bile, food remains, bubbles, etc.). Examples of computing a content score per pixel are disclosed, for example, in U.S. Pat. No. 7,567,692 to Buzaglo et al., incorporated by reference herein in its entirety. In one embodiment, a content score may be computed for each pixel of the selected patches from an input image. The areas marked 841 in content score result 804 correspond to pixels of patch 802 which received a high content score, while the areas marked 842 correspond to pixels of patch 802 which received a low content score. Similarly, areas marked 861 in content score result 814 correspond to pixels of patch 812 which received a high content score, while the areas marked 862 correspond to pixels of patch 812 which received a low content score. In these exemplary images, it is possible to see that a typical image captured in the colon may receive a higher content score and a higher white score, while a typical image captured in the small bowel may receive lower scores.

In some embodiments, other scores may be computed in addition to the content score and/or instead. For example, a "white" score may be computed for the patches being analyzed, e.g., in 806 and 816. A white score indication per pixel may correspond to, or indicate, pixel values which are substantially white. Pixels that receive a high white score indication may be correlated to intestinal content and/or bubbles, which may cause a bright reflection of the device's illumination units. Typical tissue in the gastrointestinal tract may have a reddish or yellowish hue. The white score per pixel may be calculated using an equation which determines the distance of the pixel to the "completely white" pixel. The completely white pixels are pixels which their values of RGB are (255, 255, 255).

In another embodiment, the white score may be calculated using an SVM linear classifier, with R, G and B values of the pixels in the input image as the features of the classifier. A training set for such classifier may include marking, for example by a human professional, the white areas or pixels in the image, and training the classifier according to the obtained training set.

A white score for an image may be computed based on the white score indications per pixels of the image. For example, the total number of pixels in an image which received a high white score indication, or the percentage of pixels in an image which received a high white score indication, may be used to determine the white score of the image.

Depending on the preparation procedure that the patient undergoes prior to performing the in vivo imaging procedure, the colon may contain more intestinal contents and more bubbles compared to other GI organs, for example the small bowel. Therefore, a high "white" score or rating of an image may indicate that the image was captured in the colon, while a low "white" score of an image may indicate that the image was captured in the small bowel, the esophagus or the stomach.

Figure 8:
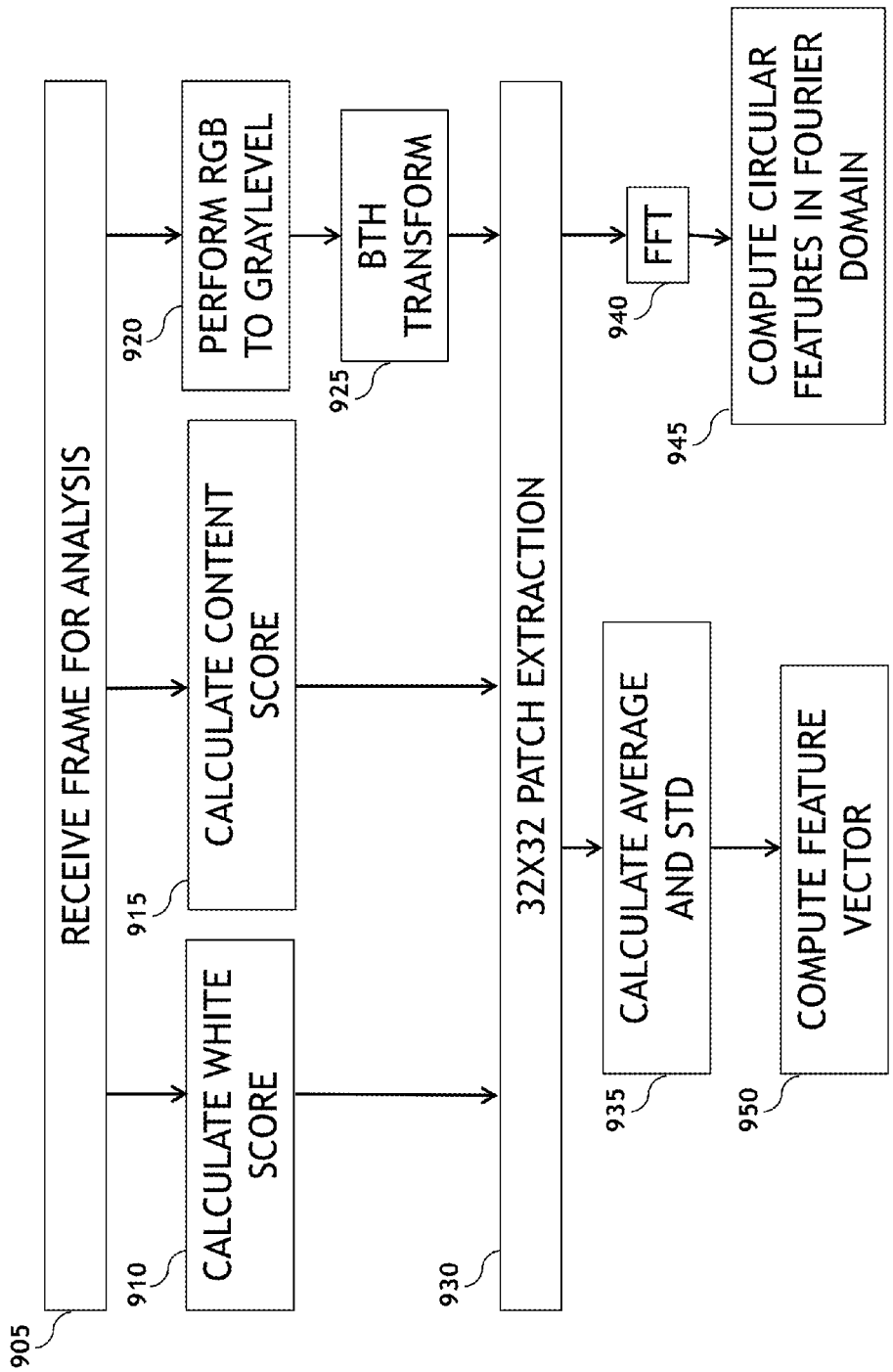
FIG. 8 depicts a flow chart of a method for computing feature vectors of in vivo images according to an embodiment of the invention.

Reference is now made to FIG. 8, a flowchart of a method for computing feature vectors of in vivo images according to an embodiment of the present invention. Different methods for classification of images into classes are known in the art, in the field of pattern recognition and computer learning. The goal of statistical classification is to use an image's characteristics to identify which class or group it belongs to. A classifier may be, for example, a linear classifier that achieves this goal by making a classification decision based on the value of a linear combination of the characteristics. In other embodiments the classifier may be non-linear. The characteristics of an image are also known as feature values and are typically presented to the classifier (e.g. processor) in a vector called a feature vector.

In operation 905, an image frame from the image stream may be received for analysis, for example may be stored in a storage unit (e.g. storage 19) which may be operationally connected to a processing unit such as processor 15. The image frame may be analyzed by computing various scores or features, and these features may be used for classification of the images to different anatomical regions or GI segments in which the images were captured. For example, a white score for the image may be calculated in operation 910, and/or a content score for the image may be calculated in operation 915. These scores may be used for calculating features of a feature vector used for classification of the images in subsequent or following operations according to embodiments of the invention. In some embodiments, the scores may be computed for the whole image or for portions thereof, e.g. only for selected patches of the image.

In operation 920, the image, which may be received in RGB (Red, Green, Blue) format, may be transformed to a gray-level (or grayscale) image, using methods known in the art. Using the grayscale image, a Top Hat transform may be performed, for the whole image or for portions thereof. For example, a Black Top Hat (BTH) transform may be applied to the grayscale image in order to enhance small details, such as villi patterns. The structuring element may be selected as a 5×5 matrix of ones. Following this transformation, each patch may be multiplied by a 32×32 2D hamming window.

In operation 930, the image may be divided into areas or patches. The patches may be equal in size and shape, for example an image of 256×256 pixels may be divided into a grid of 8×8 patches, each patch being a square of 32 pixels in length and in height. Other sizes may be selected. Several patches of the image may be selected for analysis, e.g. as described with relation to FIG. 6. For each selected patch, several parameters representing the values of pixels in the patch may be calculated. For example, in operation 935, parameters or features related to the pixel colors may be computed per patch. Exemplary features may include one or more of the following features: average and/or standard deviation of a content score of the patch, average and/or standard deviation of the white score calculated for the patch, averages of the R, G and/or B channels of pixels in the patch (wherein R represents the red pixels value of the patch, G represents the green pixels of the patch and B represents the blue pixels of the patch), and standard deviation of the Red channel. Other features may be calculated per patch, in addition to the above features and/or instead.

In operation 940, Fast Fourier Transform may be performed on one or more of the selected patches, and circular features may be computed in the Fourier domain, e.g. as described in FIG. 4 herein. A number of parameters or features representing the texture of the patches, e.g. 12 features, may be extracted and used when computing a feature vector of the patch. For example, a 2D Fast Fourier Transform may be applied on each selected patch, and the modulus of each output number may be computed, followed by a shift of the zero frequency component to the center of the patch. In order to keep the same energy for each patch, e.g. irrespective to illumination changes, the patch may be normalized to a unit length vector. Then Fourier domain features may be extracted, e.g. by averaging pixels values which are positioned on a circle which is centered at the center of the patch. A predetermined number of circles of different radii (different distances from the center) may be selected as features for the feature vector. In one example, the circles with radius of 3 pixels to 14 pixels from the center may be selected, thus providing 12 features in the Fourier domain.

The feature vector, computed in operation 950, may include color-based features such as standard deviation and average of the content score and the white score, and may also include the texture-related features extracted from the Fourier domain.

Segment analysis, which is also referred to as anatomical region analysis herein, may indicate in which segment of the GI tract an image was captured. For example, a processor such as processor 15, processor 14 or anatomical region detector 13 of FIG. 1 may determine a segment or an anatomical region in which an image was captured. In some embodiments, anatomical regions or segments may be selected for example from the following list: small bowel, duodenum, colon, esophagus, stomach, etc.

In each anatomical region or segment of the GI tract, image frames may have certain properties which may be unique to that segment. For example, villi texture may typically be found only in the small bowel anatomical region. Certain colors may be typical to the small bowel (e.g. reddish or pinkish hues) while other colors may be typical to the colon (e.g. greenish, yellowish or brownish hues, as well as white). Furthermore, since the small bowel is a relatively narrow tube compared to the wider colon, the images in the small bowel may be brighter (tissue walls are closer, thus the light is reflected with greater strength) while images in the colon may be darker. All these properties may be used to classify images as belonging to a certain segment of the GI tract, and/or to determine the point of time in the image stream in which the imaging device transitions from one anatomical region to another, e.g. from the stomach to the small bowel, or from the small bowel to the colon.

The feature vector computed in operation 950 may be used to determine a segment score per patch or per image, the segment score or rating indicating a probability, a grade or a measure that the patch belongs to an image captured in a certain (e.g, predetermined) segment of the GI tract. A segment score or rating for an image may indicate in which anatomic segment of the GI tract the image was captured. A segment score may indicate or correlate to a probability that the image was captured in a certain (e.g. predetermined or selected) portion of the GI tract, or in a predetermined segment or sub-segment of the GI tract. For example, the segment score may be high when there is a high probability or indication that the image was captured in the small bowel, and the segment score may be low if there is a high probability that the image was captured in the colon. Other values and ranges may be used, for example if the image stream is to be segmented into a plurality of segments, ranges of scores may be defined per each segment, e.g. a stomach segment may receive segment score values in the range of 0-2, a small bowel segment may receive segment score values in the range of 3-5, and a colon segment may receive segment score values in the range of 6-8. Other ranges and other values may be used, e.g. images captured in the small bowel may receive positive segment score values, while images captured in the colon may receive negative segment score values.

Figure 9:
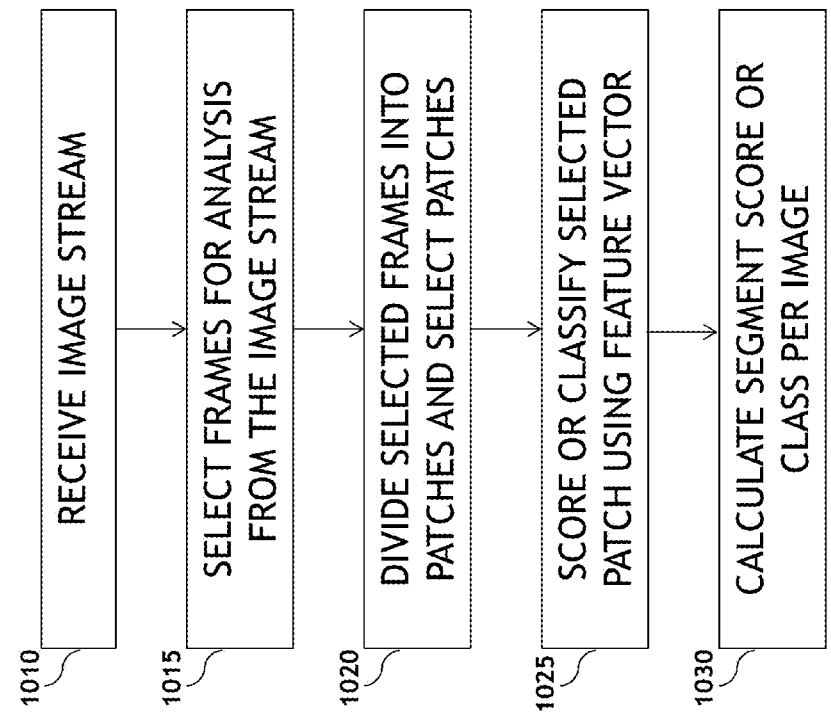
FIG. 9 depicts a flow chart of a method for computing a segment score according to embodiments of the invention.

Reference is now made to FIG. 9, a flowchart of a method for computing a segment score for a stream of in vivo images according to embodiments of the invention. In operation 1010, a stream of images captured by an in vivo imaging device may be received, e.g may be recorded and stored in a storage unit operationally connected to a processing unit. In operation 1015, a subset of images or frames from the image stream may be selected for GI tract segment analysis. For example, one out of every predetermined number of captured frames may be selected for segment analysis. In one example, 2,000 images may be selected from the image stream, e.g. one out of every 100 images may be selected in a sequence of 200,000 sequentially numbered frames in the received image stream. For example, frame index numbers 1, 101, 201, etc. may be selected. The selected subset of frames may be re-numbered with new frame index numbers in order to simplify the next calculations, for example the selected subset of frames may be renumbered from 1 to 2,000.

Other methods may be used to select frames for segment analysis, for example selecting a frame captured every fixed (predetermined) time interval (e.g. dividing the image stream to ten-minute intervals, and selecting one frame captured from each interval). The selected frames may be random frames selected from the predetermined time interval, or in another example a first frame captured in each predetermined time interval of the image stream may be selected for segment analysis. If the imaging capsule used to capture the image stream includes multiple imaging systems, images for analysis may be selected from one imaging system or from more than one (e.g. for example, one image for segment analysis may be selected from a first imaging system and the next image for segment analysis may be selected from an alternate imaging system).

In operation 1020 the selected frames may be divided into patches, e.g. as described in FIG. 6 above. Certain patches from each selected frame may be selected, e.g. according to predetermined parameters which may be based on color properties, or according to a predetermined region of the image which may be determined as the region of interest (ROI). In one example, the peripheral patches may be discarded from the segment analysis, since they are not within the predefined region of interest in the images.

The selected patches may then be classified to an anatomical region in operation 1025. The classification may be based on a feature vector extracted from the selected images, e.g. a feature vector calculated as described in operation 950 of FIG. 8. The feature may be normalized, for example each feature may be normalized to mean which equals zero and variance which equals one.

The classification may be performed using classifiers which are known in the art, for example a classifier such as an SVM (Support Vector Machine) classifier may be used if the images are segmented into two classes, e.g. small bowel images and colon images. Given a set of training examples, each marked as belonging to one of two categories (e.g. anatomical regions), an SVM training algorithm builds a model that assigns new examples into one category or the other. An SVM model is a representation of the examples as points in space, mapped so that the examples of the separate categories are divided by a clear gap that is as wide as possible. New examples are then mapped into that same space and predicted to belong to a category based on which side of the gap they fall.

According to one embodiment, the classifier may be trained using a labeled training set of in vivo images captured in the small bowel and in the colon. Each in vivo image in the training set may be labeled, for example by a human professional, as belonging to the first class (e.g. small bowel region) or to the second class (e.g. colon region). An RBF kernel (radial basis function kernel used in support vector machine classification) may be used in one embodiment and a 10-fold cross-validation technique may be used for choosing the best hyper-parameters C (coefficient indicating how much weight the training set should be given in the SVM optimization formulation), Gamma (parameter in the RBF kernel). The classification error criteria may be defined as:

$$1 - froc\_curve \quad (eq. 1.1)$$

The training phase of the classifier may be used to determine the parameters and support vectors of the classifier, e.g. the values of $SV_i$ and $\alpha_i$ in the following equation:

$$soft\_margin(x) = \Sigma_{i=1}^{n}(a_i k(x, SVi) + b) \quad (eq.1.2)$$

wherein $k(x_i, x_j)$ indicates the kernel function, n is the number of support vectors, and b is the bias coefficient.

Next, a feature selection operation may be performed, for example in a greedy manner. In one example, both backward elimination and forward selection methods may be used. According to the results of the selection operation, the final set of features used in the classifier may be selected. In some embodiments, a set of all Fourier-domain features as well as color-based features listed above may be selected.

Once the classifier is determined (e.g., the list of features of the feature vector is defined, and the classifier is trained using a training set of labeled images), each selected patch may be classified, e.g. a score may be determined for each of the selected patches of an image, whether the patch is likely to belong to a small bowel segment or to a colon segment. For example, a high score may be assigned to patches which were likely captured in the small bowel, and a low score may be assigned to patches which were likely captured in the colon. In one example, a small bowel patch may receive the value of "1", while a colon image may receive the value of "0". Other classes or segments may be used, and different ranges of scores may be used.

After each patch is classified and scored, a segment rating or score may be calculated or determined per image (operation 1030). The segment score may include, for example, a linear or non-linear combination of the scores calculated per patch. In one embodiment, the scores per patch may be summed, and the total score may be the image segment score. For example, if 12 of the selected patches in an image received a small bowel classification and were assigned the value "1", and 24 of the selected patches of the image received a colon classification and were assigned the value "0", the image segment score will be 12.

Figure 10:
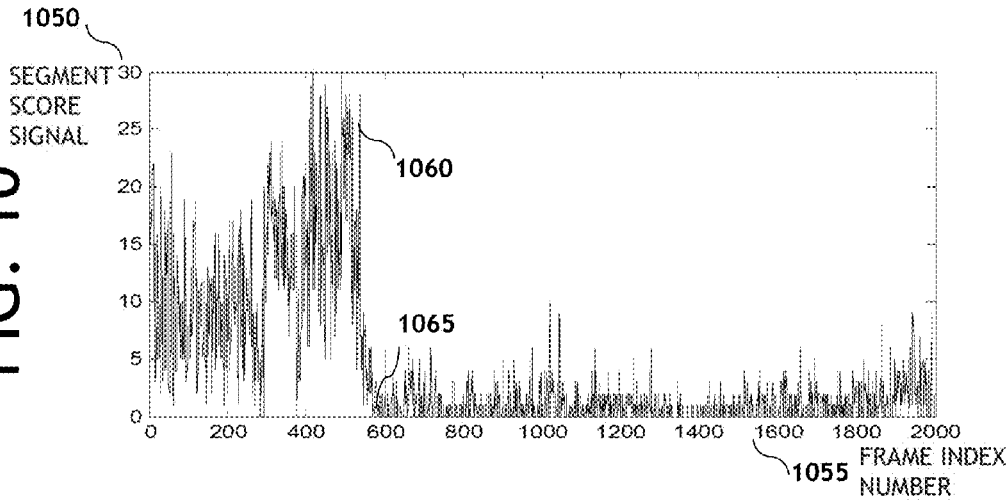
FIG. 10 depicts an exemplary segment score function for images of an in vivo image stream according to an embodiment of the invention.

Reference is now made to FIG. 10, which depicts an exemplary segment score function for images of an in vivo image stream. The segment score signal, curve or function, when referred to herein, indicates the function created by calculating the segment scores for selected images from the image stream. Y-axis 1050 indicates the segment score value that each image was assigned as a result of a classification operation, e.g. as described in FIG. 9. The minimal segment score assigned to an image in this example was zero, and the maximal segment score assigned to as image was 32, which is the number of patches selected from the image. X-axis 1055 indicates a frame index number, for example a sequential number of the selected image, from a total of e.g. 2,000 images selected for segmentation analysis from the image stream. The segment score function or signal is indicated by line 1060. It is noted that the total number of images selected for analysis may be any other predetermined number of frames, and any other range of values may be used for calculating the segment score.

Point 1065 indicates a step or increment which was identified in the segment score function. As shown in the graph of FIG. 10, the segment score values assigned to the images with frame index number in the range of 0-600 have a mean value of ~15. The segment score values of the images with frame index number in the range of 601-2,000 have a mean value of ~2. The step or increment is therefore detected at X=600, where the mean value of the segment score function has a substantial drop, maximal decrease or sudden decrease in value. This step is a down-step, which indicates a substantial decrease in the segment score function values. A substantial change, or a substantial increase or decrease, may be a change, increase or decrease where the rate of change, increase or decrease (e.g., the derivative or slope of the curve) is greater by some threshold than the rate of change surrounding the point or area of the substantial change. A substantial change may be a maximal change or maximal difference between the values, sum values, or mean values of the segment score function, calculated for example for images selected for analysis before a candidate point of transition and after it. For example, each image in the stream or selected images may be candidate points of transition between segments of the GI tract. For each image or for the selected images, the difference between values based on the segment score function may be computed. For example the difference between a sum or mean of the segment score values of a predetermined number of images (e.g. 100 images) captured before the candidate point and a sum or mean of the segment score values of the predetermined number of images (e.g. 100 images) captured after the candidate point of transition may be computed. The candidate point for which a maximal difference was computed may be determined as the point of substantial change or point of maximal change, and therefore identified as the transition point between organs or segments of the image stream. In some embodiments, e.g. when the values of the segment score function are typically lower in a first segment and higher in a subsequent segment of the image stream, the detected step may be an up-step, which indicates a sudden increase in the mean values of the segment score function.

Reference is now made to FIG. 11, a flowchart of a method for determining a step or increment in a segment scores function, according to one embodiment of the invention. In operation 1145, a frame segment score may be calculated for selected frames of an image stream. The frame segment score may be calculated, for example, as disclosed in the flow chart of FIG. 9 above. In operation 1150, a smoothing function such as a filter (e.g. a median filter) may be applied to the segment scores to receive a smoothed segment score function (or signal).

In operation 1155, a global step may be detected in the smoothed segment score function. The global step may be defined as a substantial change in the segment score function values, for example an abrupt, notable, detectable, or maximal change (e.g. increment, step, jump, difference or shift) in a parameter calculated based on the segment score signal, function or curve, e.g. the sum or mean level of the segment score signal, function or curve or segment score signal values. The global step indicates a sudden, for example maximal, transition in the values of the segment score signal (or in a parameter calculated based on the segment score values), and may correlate to a transition in the image stream of the imaging device from a first organ or anatomical region to a subsequent organ or anatomical region (e.g. a transition of the imaging device from the stomach to the small bowel, or from the small bowel to the colon). A global step may be an up-step or a down-step, depending on the scoring method used to compute the segment score function. If the values assigned to a first segment in the image stream are typically lower than the values assigned to a second segment of the image stream, the global step is an up-step, which indicates an abrupt increase in the mean-level of the segment score signal values. Similarly, if the values assigned to a first segment in the image stream are typically higher than the values assigned to a second segment of the image stream, the global step is a down-step, which indicates an abrupt decrease in the mean-level segment score signal values. In some cases, more than one global step may be detected in the segment score signal, and the detected steps may be up-steps and/or down-steps.

In order to detect a global step, the entire segment score signal may be considered (e.g., segment score values of all the frames selected for analysis may be considered). In one embodiment, a single down-step which splits the segment score signal into two parts may be detected as the global step, where the left part of the segment score signal has a high average segment score, and the right part of the segment score signal has a low average segment score, and wherein both the right and the left parts have a small variance. This can be formulated as an optimization problem, e.g.:

$$g(x) = E(\text{left}[x]) - E(\text{right}[x]) + \alpha(\text{Var}(\text{left}[x]) + \text{Var}(\text{right}[x]))$$

$$x_{glob} = \arg\min \{g(x)\} \quad (\text{eq. 2})$$

where $E(x)$ is the expectation function, $\text{Var}(x)$ is the variance function, $\text{left}[x]$ includes all the frames that come before frame index number x in the segment score signal, and right $[x]$ includes all the frames that come after frame index number x in the segment score signal.

The optimization problem may be defined as minimizing $g(x)$, or alternatively maximizing $-g(x)$. The constant parameter $\alpha=0.4$ may be determined empirically. $x_{glob}$ is the frame index number of the detected global step in the smoothed segment score signal. In some embodiments, the global step may be an up-step instead of a down-step. It is noted that although in some embodiments the detected global step may be sufficient to detect the transition of an imaging device from one organ to another, relying only on the global step may prove insufficient in some cases.

In operation 1160, a local step may be detected in the segment score signal. The local step may be detected in predetermined segments, windows (e.g., a series of images, the series of a certain length shorter than the image stream) or intervals of the segment score signal (or its corresponding smoothed function), e.g. intervals that do not include the entire segment score signal. A local step may indicate a substantial or maximal change in a parameter calculated based on a predetermined interval of the segment score signal e.g. a mean level of values in a predetermined window, segment or interval of the of segment score signal. For example, the local step may be the steepest edge detected in a portion of the signal. In one embodiment, an edge with the highest or maximal score value along the segment score signal may be detected as the local step, in a portion or window of a certain length, the window including a predetermined range of values from the segment score signal. In one example, each window or interval may include a portion of the segment score signal comprising a predetermined number of frames before and/or after the current frame being considered. In another example, each interval used for detecting a local step may include a predetermined time period from the image stream, e.g. frames captured within a time period of 15 minutes may comprise one interval. The intervals or windows may or may not overlap each other.

The local step detected may be an up-step or a down-step. A local down-step is a step that indicates a substantial or maximal decrease in a parameter calculated based on a predetermined interval of the segment score signal, e.g. a mean level of values in a predetermined interval of the segment score signal or the smoothed segment score signal. A local down-step may be detected in a signal if the values of the segment score signal are typically higher in a first segment of the image stream and typically lower in a subsequent segment. The local step indicates a local transition in the values of the segment score signal, and may correlate to a transition in the image stream of the imaging device from a first organ or anatomical region to a subsequent organ or anatomical region (e.g. a transition of the imaging device from the stomach to the small bowel, or from the small bowel to the colon). In some embodiments, a local up-step may be detected. The length of the interval or window which is used to compute the local step may vary according to amount of data in the signal and according to the smoothness of the signal.

In one embodiment, in order to detect the local step, a local step function l(x) may be computed as a convolution with, e.g. a down-step function, in a window of a predetermined length of L frames, e.g. 140 frames In order to compute the local step function l(x), frames of the interval or window may be selected for example either before the current frame or after it. In other embodiments, half of the frames in the interval (e.g. 70 frames in the following example) may be selected before the current frame, and the other half may be selected after the current frame. For example, in order to compute a local step function value for frame index x in the smoothed segment score signal, 70 values to the left of frame x may be summed, and from this sum 70 values to the right of frame x may be subtracted, for example as in the following function:

$$l(x) = \sum_{k=x-70}^{x} f(k) - \sum_{k=x+1}^{x+70} f(k) \qquad \text{(eq. 3)}$$

where l(x) indicates the local step function (which may also be referred to as a local edge function or local edge signal), and f(k) indicates the segment score function. In order to obtain the best local step, l(x) should be maximized.

In another example, in order to detect a local step, the segment score of a sequence of images in a predetermined image sequence interval or time period, may be averaged based on image segment scores of the current image and its neighboring or adjacent images in the sequence. The segment score local step function may be defined as, for example, an average of the segment scores per image, averaged over a predetermined number of consecutive or adjacent images. For example, the segment score may be calculated by averaging the segment scores of the current image and 70 previous images. Thus the local step value for current image frame x may be computed as an average of the segment score of scores of a predefined number of frames before frame x plus (or minus) the current image x and average of the segment scores of a predetermined number of previous and/or next images. The segment score of frame x need not necessarily be included in the computation of the local step value.

In some embodiments, more than one local step may be detected, and the detected local steps may be up-steps, down-steps, or a combination thereof.

In some embodiments, the detected local step and the detected global step may be combined (operation 1165) into a single combined step function h(x), and the combined step function h(x) may be optimized, for example:

$$h(x)=l(x)-c*g(x) \qquad \text{(eq. 4)}$$

$$x_{max}=\max(h(x)). \qquad \text{(eq. 5)}$$

Calculating $x_{max}$, the maximum of h(x), will result in a combined step detection which considers both the global step and the local step detected. A constant c may be chosen empirically to provide the best results for a given training set. The combined step detection may result in a single frame index number $x_{max}$, the frame index number representing a point of transition of the imaging device from a first anatomical region to a subsequent anatomical region.

In some embodiments, the images used for the segment analysis are only images which have been selected for analysis, e.g. in step 1015. Therefore, in embodiments in which not every image is analyzed, a set of "consecutive" images in the segment score function may include images which are not immediately sequential in the original image stream received from the capsule 40. The images may be consecutive or adjacent images, or neighboring images in the originally captured image stream, but in some cases there may be gaps between the images being averaged, for example if not all images from the original image stream are selected to be analyzed or processed for segmenting the image stream according to anatomic landmarks or organs.

In operation 1170, a transition in the image stream may be determined. For example, based on the result of the combined step detection in operation 1165, or based on a combination of the local and global increments, jumps or steps, e.g. by maximizing the combined function h(x), the point of transition may be determined to occur in frame index number $x_{max}$ (correlating to the detected combined step). The frame index number in the original image stream which corresponds to $x_{max}$ may be determined as a frame indicating a transition from one organ (or anatomical segment of a GI tract) to another in the image stream, e.g. a first cecal image when the transition is determined from the small bowel segment to the colon segment in a GI tract imaging procedure.

Figure 12:
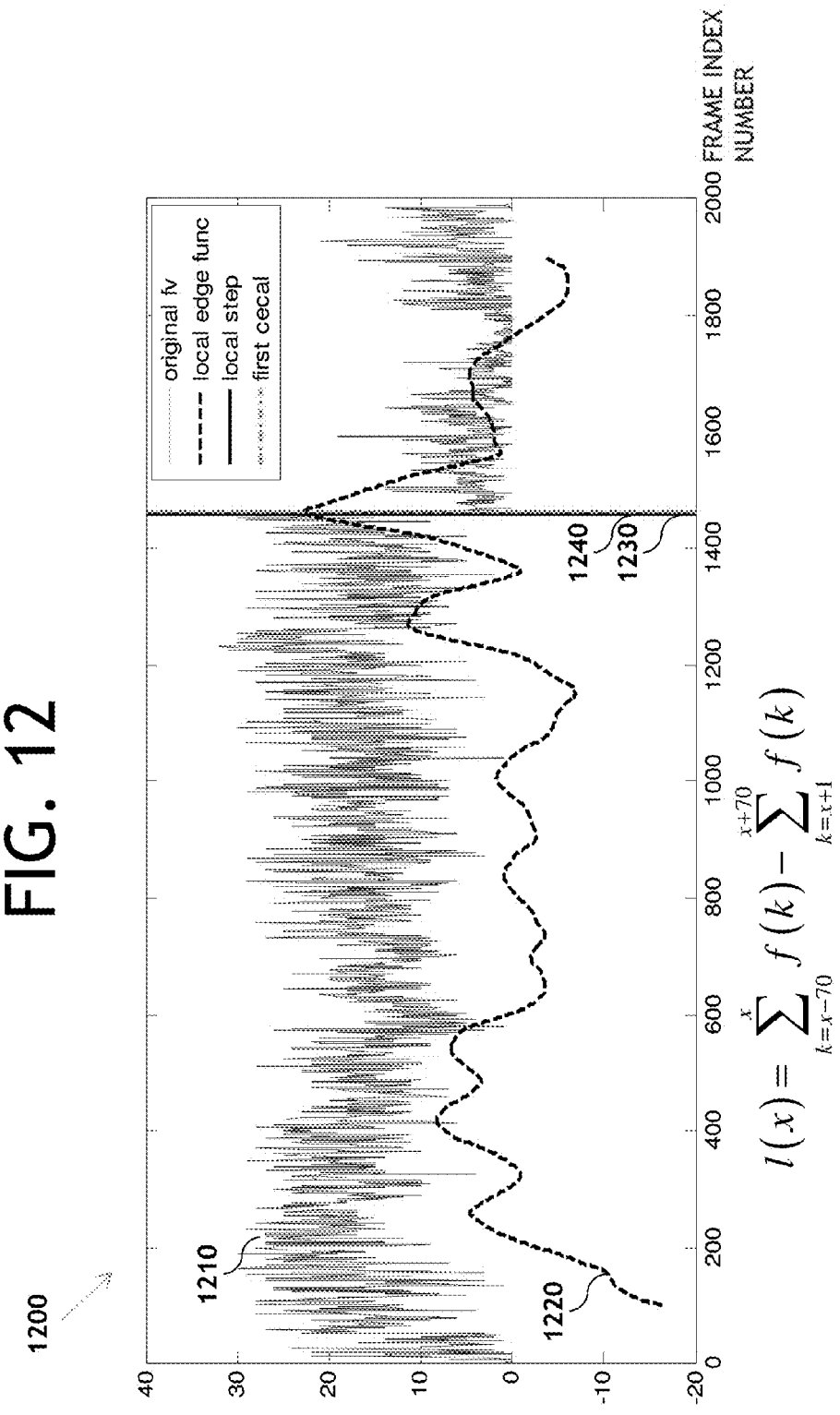
FIG. 12 depicts a graph of a segment score function according to an embodiment of the invention.

Reference is now made to FIG. 12, which depicts a graph 1200 of a segment score function according to an embodiment of the invention. Line 1210 indicates the segment score function values, for 2000 selected images of an image stream. The images are numbered according to their sequence number in the set of selected images, from 1 to 2000. The local step function is calculated as described in operation 1160 above, and the resulting values are indicated by line 1220. It is noted that the line 1220 starts at frame index number 71 and ends at frame index number 1830, since the local step score is computed for a window of 70 frames from each side of each image in the graph. Line 1230 indicates the maximum value of the local step function, e.g. the local step detected in graph 1200. Line 1240 (which is located in the same position as line 1230) indicates the actual first cecal image, or the transition point in the image stream, from the small bowel to the colon.

Figure 13:
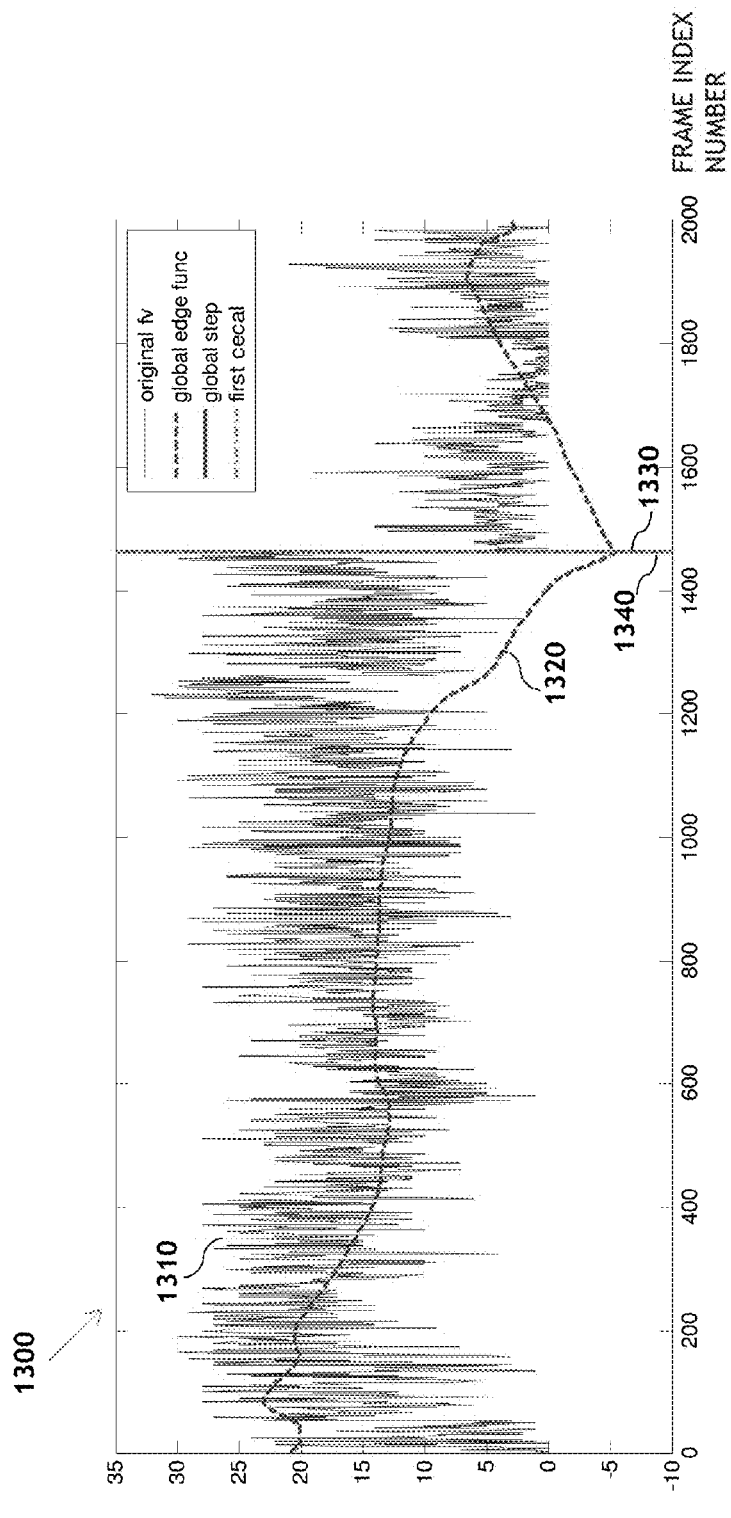
FIG. 13 depicts a graph of a segment score function according to an embodiment of the invention.

Reference is now made to FIG. 13, a graph 1300 of a segment score function according to an embodiment of the invention. Line 1310 indicates the segment score function values, for 2000 selected images of an image stream. The images are numbered according to their sequence number in the set of selected images, from 1 to 2000.

Line 1320 indicates the global step function calculated for the given segment score values of this graph. The minimal value of the global step function is indicated by line 1330, which is the detected global step in this example. The transition point of the imaging device in this image stream from the small bowel to the colon is indicated by line 1340, which is the first cecal image. It is noted that in this example, the detected global step and the actual transition point in the image stream are united.

Reference is now made to FIG. 14A and FIG. 14B, graphs of segment score functions according to an embodiment of the invention. Graph 1400 of FIG. 14A includes a segment score function 1410, a local step function 1420, a global step function 1430, and a combined function 1440. The detected local step is marked by line 1460, and the detected global step is marked by line 1450. The detected step of the combined function is marked by line 1450 as well. In this example, the global step and the combined function step are positioned at the same frame. The actual position of the transition in this image stream occurs close to the step of the combined function, marked by line 1470.

Graph 1401 of FIG. 14B illustrates another example, in which the local step and the step of the combined function are the same. A segment score function 1411, a local step function 1421, a global step function 1431, and a combined function 1441 are marked within graph 1401. The detected local step is marked by line 1461, and the detected global step is marked by line 1451. The detected step of the combined function is marked by line 1451 as well. In this example, the local step and the combined function step are positioned very close to each other, e.g. substantially at the same frame. The actual position of the transition in this image stream occurs close to the step of the combined function, marked by line 1471.

Reference is now made to FIG. 15, which illustrates phases of a method for bubble detection according to an embodiment of the invention. Bubbles are often found in the GI tract, and may occlude the imaged scene. Such occlusion may vary the segment score, for example the bubbles may occlude a villi area in the small bowel, and cause the segment score to be indicative of a colon segment instead of a small bowel segment. This may cause identification of premature steps or false alarm steps, when trying to find a point of transition of the imaging device from one GI segment to another, e.g. from the small bowel to the colon. For example, when calculating the global step function, the local step function, or the combined function for detection of a transition in an image stream, as a result of the bubbles in the images which may hide or obscure the underlying tissue, the detected step may not be the true point of transition in the image stream.

In FIG. 15, image 1510 is an in vivo image captured in the small bowel. However, this is not apparent, and may be difficult to deduce, due to the large area of bubbles 1511 which appear in the image. In order to compute the area of bubbles in an image (or a score corresponding to the amount of bubbles in an image), image 1520 may be obtained from image 1510, by applying an operation of white top-hat transform and/or black top-hat transform, e.g. in order to emphasize the textural features of the bubbles which are small white circles. After the top-hat transform, the obtained image 1520 is in gray-level.

Image 1530 shows image 1520 after a thresholding operation for segmenting the image, e.g. in order to create a binary image and extract the area of bubbles (or elements of round white shapes in the image which correspond to bubbles). The thresholding operation includes setting a threshold for segmenting the image. Image segmentation, typically used to locate objects and boundaries in images, is the process of partitioning a digital image into multiple segments or multiple sets of pixels, in order to simplify and/or change the representation of an image such that it is easier to analyze. Segmentation of the image, when referred to herein, includes dividing the image into separate portions, wherein each portion has a specific characteristic. For example, a portion of the image which includes bubbles may comprise one segment, and a portion of the image without bubbles may comprise a separate segment.

In order to extract an area of bubbles in an image, after assigning the gray-level value, it is determined whether the pixel should be black or white in the result segmented image 1530, by comparing to the predetermined threshold for segmenting the image. E.g., if the pixel value is above the predetermined threshold, the pixel will be assigned a white value (e.g. 1), otherwise the pixel will be assigned a black value (e.g., 0). In image 1530, region 1531 of the image (which includes bubbles) was assigned a white value, while the rest of the image (or at least the rest of the image inside the ROI) which does not include bubbles (area 1532) is black.

Morphological operations may be performed on image 1530 in order to find the area of the image which includes a white value. A bubble score may be calculated per image, the bubble score being a measure which indicates the amount or relative amount of bubbles in the image 1510 (or in a portion thereof, e.g. in a Region of Interest 1535 of the image). For example, the following equation may be used to calculate the bubble score of an image:

$$BubbleScore = \frac{numBubblePixelsROI}{numPixelsROI} \quad \text{(eq. 6)}$$

where numBubblePixelsROI indicates the number of pixels in the predetermined region of interest of an image (ROI 1535) which were detected as pixels depicting bubbles (number of pixels in area 1531 of the image), and numPixelsROI indicates the total number of pixels in the ROI 1535 of the image (number of pixels in area 1531+number of pixels in area 1532 of the image, both included within the circle 1535 which indicates the ROI).

Reference is now made to FIG. 16A, a flow chart of a method for determining a transition point in an image stream, the image stream including at least one bubble sequence, according to one embodiment of the invention. A bubble sequence, as referred to herein, is a sequence of images, in which each image of the sequence contains at least a certain predetermined amount of bubbles. If the image stream includes a bubble sequence, it may be determined that bubbles may hide the actual transition in the image stream (e.g., if the transition occurs in frames which include a large area of bubble). In such cases, the transition point which was earlier determined based on the combined step function, may be corrected using the following operations.

In operation 1610, a bubble sequence may be detected. Detecting a bubble sequence may include determining a bubble score for each image (or at least for each image selected for segment analysis). After the bubble score determination, a local bubble edge score may be computed for at least a portion of the selected images. The local bubble edge score may be computed, for a selected current image, by summing the bubble scores for a predetermined number of images before the current image and for a predetermined number of images after the current image (which may be the same number as the predetermined number of images before the current image, or different). The predetermined number of images may be any natural number, for example 10, 25, 50, 70 etc.

In order to determine the bubble sequence, an optimal step may be detected in the local bubble edge signal, which is a function with the values of the local bubble edge scores for each image. For example, an optimal up-step may be detected using the local bubble edge signal, e.g. by maximizing $-l(x)$ (e.g as shown in eq. 3) for the bubble score signal, and then detecting an optimal down-step after the up-step, e.g. by maximizing $l(x)$ for the bubble score signal. Then the two detected maxima points may define a candidate bubble sequence, which may further be determined as a bubble sequence by checking certain conditions. One example condition may include checking that the candidate bubble sequence length is longer than a predetermined threshold, e.g. at least 4% of the image stream length. Another example condition may include checking that the average bubble score for each image in the candidate bubble sequence is larger than 50% (e.g. larger than 0.5, if the score is normalized to the range of [0,1]). Further, another condition may include checking if at least a predetermined amount of the images in the sequence were assigned a bubble score which is larger than the average bubble score in the sequence. For example, 40% of the images in the bubble sequence must have a bubble score which is higher than the average bubble score for the images in the bubble sequence. In some embodiments, if one or more of these conditions are true, the candidate bubble sequence may be determined as a bubble sequence. It is noted that in some embodiments, only a portion of these conditions may be checked. Other predetermined thresholds and conditions may be used.

In operation 1615 a local step may be detected in the local step function of the segment score signal. Detecting the local step may include detecting a down-step in the local step function of the segment score signal. After the down-step is detected, the next up-step may be detected. The sequence of images between the detected down-step and the next up-step may be determined as a low segment score sequence in operation 1620. In this embodiment, the low segment score sequence may include a sequence of image frames with relatively low segment score values, compared to other frames in the vicinity of the sequence (e.g. a certain number of sequential frames adjacent to the low segment score sequence). In other embodiments, the segment score signal values may be typically lower at a first segment of the GI tract, and higher in a following segment. In such cases, detecting the local step may include detecting first an up-step and then a down-step, thus the low segment score signal may include a sequence of image frames with relatively high segment score values.

In operation 1625, an intersection or overlap between the bubble sequence and the low segment score sequence may be determined. The intersection or overlap may be determined if frames with the same frame index number are included in both the bubble sequence and the low segment score sequence. If the detected intersection region is sufficiently large, e.g. larger than a predetermined threshold of, for example, 100 selected images, in operation 1630 a next down-step may be detected in the segment score signal, after the local up-step. If the detected down-step is smaller than a predetermined threshold (operation 1635), then the middle of the bubble sequence may be determined as a transition point in the image stream, e.g. as a first cecal image in the transition from the small bowel to the colon (operation 1645). Otherwise (the detected down-step is equal to or larger than a predetermined threshold), the next down-step is determined as the transition point in the image stream, e.g. as the first cecal image (operation 1640).

Figure 16B:
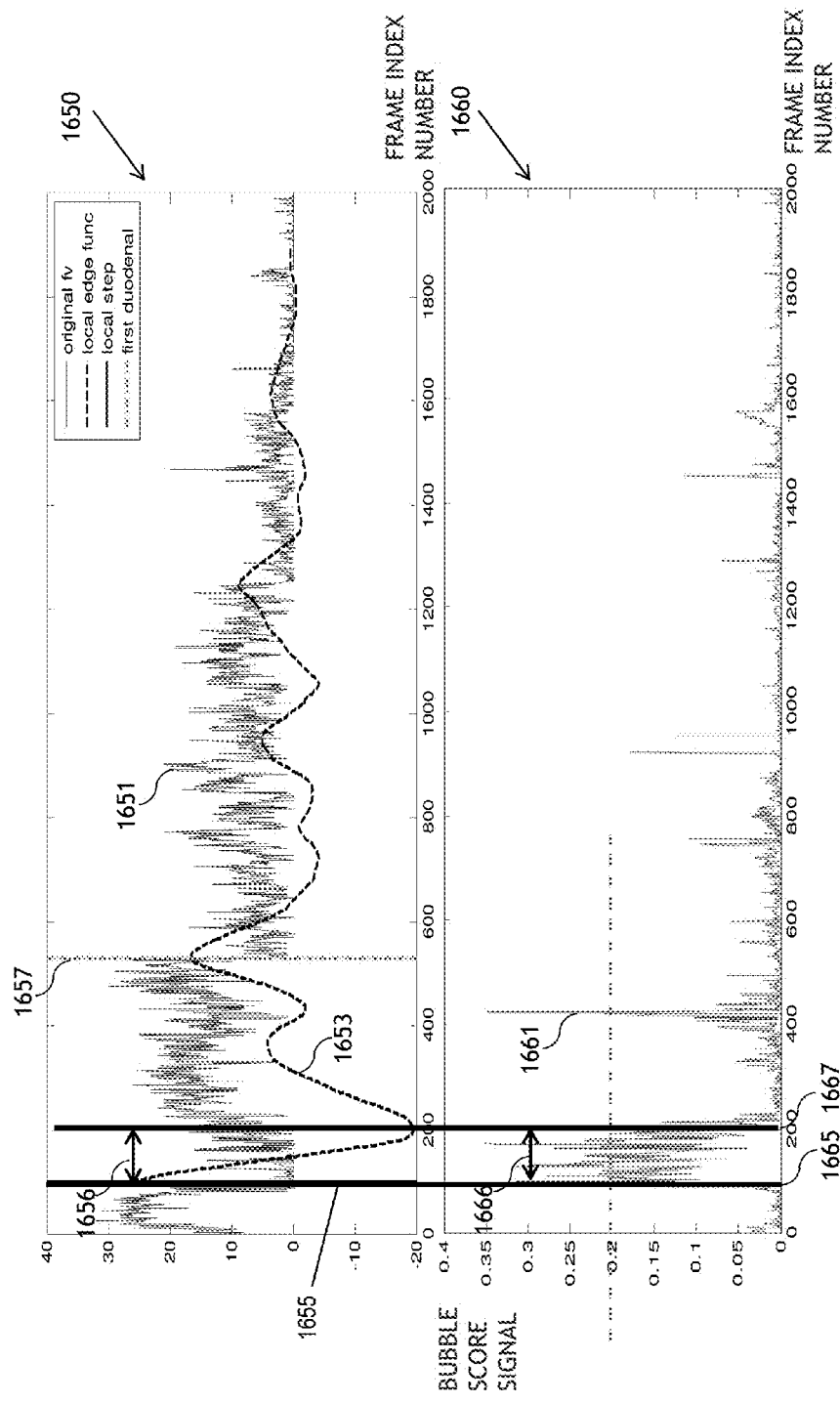
FIG. 16B includes an exemplary segment score signal and an exemplary bubble score signal according to an embodiment of the invention.

Reference is made to FIG. 16B, which includes an exemplary segment score signal 1651 in graph 1650, and a bubble score signal 1661 in graph 1660. The x-axis indicates the image frame index number, sequentially numbered in the set of frames selected for segment analysis from the image stream. A bubble sequence 1666 is detected between frame index number 100 (1665 in graph 1660) to frame index number 200 (1667 in graph 1660), for example according to the method described in operation 1610. A low segment score sequence 1656 is detected in the interval located between line 1665 and 1667, for example according to the method described in operation 1620.

The transition between the small bowel and colon, which was detected using the combined signal, is indicated by line 1655. However, line 1655 is located in the intersection region of the low segment score sequence 1656 and the bubble sequence 1666. The actual transition point in the image stream, determined by a health care professional, is marked by line 1657.

Reference is now made to FIG. 17, which includes a method of determining a transition point in an image stream according to an embodiment of the invention. It is noted that when an in vivo imaging device such as a capsule endoscope passes from the small bowel to the colon (e.g. upon entering the cecum), the diameter of the surrounding space should become wider, since the diameter of the colon is significantly larger than the diameter of the small bowel. Therefore, an estimation of the amount (or actual area) of tissue in a scene which was captured in an in vivo image may provide an indication of the surrounding space of the device—if the device images a relatively small amount of tissue, it is probably closer to the tissue and therefore it may be deduced that the image was captured in the small bowel, where the tissue walls are quite close to the imaging device. On the other hand, if the imaging device transits to a larger space, the tissue walls are positioned further from the imaging dome, and the amount or area of tissue that is captured in a scene imaged by the device is relatively large. A score which indicates an amount or an actual area of imaged tissue in a captured scene is defined as a tissue area score (TAS). The TAS, correlating to tissue area imaged or visible in an image, may be determined by, for example, an estimated distance of the imaged object from the imaging system at the time the image was captured, and the known optical characteristics of the lens(es) in the imaging system. An estimation of the distance of the imaged tissue from the in vivo imaging device at the time the image was captured may be performed, e.g. based on brightness of areas in the image, and an approximation model or tissue structure model may be determined for the imaged in vivo tissue or organ's structure. A tissue area score or rating may be assigned to an image based on the estimated or calculated tissue area.

Since the area of tissue which is captured in a colon image is typically larger than the area of tissue captured in a small bowel image, the TAS of a small bowel image is typically lower than the TAS of a colon image.

The TAS signal may be obtained by calculating the TAS score for a set of images, e.g. for the images selected for analysis. According to an embodiment of the invention, a jump, step or abrupt change detected in the TAS signal of the images selected for analysis may indicate a transition of the imaging device from the small bowel to the colon. In other embodiments, other scores may be used to estimate the actual amount or area of tissue captured in a certain image. For example, a measure of the brightness of an image may correspond to the organ in which the image was captured. When the image is brighter, for example, the tissue walls may be closer to the imaging device and the illumination may be reflected more strongly back to the imager.

Therefore brighter images may correspond to the small bowel region, which is narrower than the colon region of the GI tract. On the other hand, when the image is darker, the tissue walls may be further from the imaging device and it may be concluded that the image was captured in the colon. Other measures or scores may be used.

In operation 1710, a TAS may be determined for the frames selected for segment analysis, and a TAS signal may be obtained. The TAS signal may be smoothed in operation 1715, e.g. using the following formula:

$$TAS(x) = avg_w(TAS(x)) + var_w(TAS(x)) \qquad (eq. 7)$$

where w is a window of a predetermined length, e.g. 10 frames, avg indicates the average and var indicates the variance of the TAS in the window.

In operation 1720, an up-step may be detected in the smoothed TAS signal.

A decision whether to use the segment score signal or the TAS signal to detect a transition in an image stream may be based on a measure of the segment score signal noisiness.

Determining a noisiness level of the segment score signal (operation 1725) is detailed, for example, in operations 1800-1830 of FIG. 18A herein. The noisiness level of a segment score signal may be a measure of the signal's jumpiness, or an indication if it is characterized by sudden jumps. A high noisiness level of a signal may indicate unpredictable values of the segment score signal. The noisiness level may be correlated to the reliability of the segment score signal for segmenting the image stream. Noisiness of a segment score signal may indicate, for example, that certain characteristics of the captured images are not as expected. For example, certain features which are used to obtain the segment score may be unreliable or may produce random or unpredictable results, and therefore carry no useful information for segmenting the image stream. In one example, if the villi structures of the GI tract are reduced or damaged due to a disease or pathology, the resulting segment score signal may be noisy.

If the segment score signal is determined to be noisy (e.g. having a high noisiness level, or a noisiness level above a predetermined threshold), the segment score signal may be considered unreliable for use in segmenting an image stream, or in detecting a point of transition in an image stream. In such cases, the TAS signal may be used to detect the point of transition of the in vivo imaging device, e.g. from the small bowel to the colon. In operation 1730, the detected up-step in the TAS signal may be determined as a first cecal image (or as the transition point in the image stream from the small bowel segment to the colon segment). If the segment score signal is determined to be clean (e.g., having a low noisiness level, or a noisiness level below a predetermined threshold), it is used to detect the transition of the in vivo imaging device from the small bowel to the colon.

Reference is now made to FIG. 18A, which includes a flow chart of a method for determining noisiness of a segment score signal, according to one embodiment of the invention. It is noted that this method may be used to determine the noisiness of other signals and/or functions described herein. The method described in the flow chart of FIG. 18A includes a set of operations which may be used to perform operation 1725 of FIG. 17.

In operation 1800, the local step function of the segment score signal may be calculated according to embodiments of the present invention, e.g. as described with relation to FIGS. 11 and 12. The result of the local step function of the segment score signal may be normalized to a range of values, e.g. between zero to one. In operation 1810, two largest local maxima points ($m_1$ and $m_2$) may be determined in the normalized signal, and relative distances, (e.g. dist parameter in eq. 9) between frames may be determined. The relative distance dist may be measured, for example, by finding the absolute number of frames between the two maxima points, divided by the total number of frames selected for segment analysis.

Next, in operation 1820, a noisiness level or measure NOS may be calculated, e.g. based on the local maxima values and the relative distances as follows:

$$ratio = \frac{m_1}{m_2} \in [0, 1] \quad (eq. 8)$$

$$dist = \frac{abs(id(m_1) - id(m_2))}{nFrames} \quad (eq. 9)$$

$$NOS = ratio * dist \quad (eq. 10)$$

In operation 1830, based on the computed value of the noisiness measure NOS, it may be determined whether the segment score signal is noisy. For example, if the value of the noisiness measure is in a predetermined range, or higher than a predetermined threshold, it may be determined that the segment score signal is noisy.

The segment score may be noisy or unclean, for example, if the patient being examined has a certain GI disease which damages the villi structures of the intestine (e.g. inflammatory bowel diseases such as Crohn's disease, ulcerative colitis or pancolitis). In such cases, the villi structures of the intestine are damaged, and may be non-existent in severe cases. Since the segment score is affected by detected villi structures, damaged villi in the GI tract may cause a jumpy, noisy or unclean segment score signal. When the segment score signal is determined as noisy, it may be unreliable to segment the image stream based on it. Therefore, other methods may be used for determining a transition point in the image stream in these cases, for example using the TAS score described herein.

Reference is now made to FIG. 18B, which depicts a graph 1850 of a segment score signal, and a graph 1860 of the local step function 1791 corresponding to the segment score signal 1781 according to an embodiment of the invention. It is noted that the local step function values are normalized in this example to the range of [0,1]. In graph 1860, local maxima 1793 (in frame index number 118) and local maxima 1792 (in frame index number 1291) of the segment score are determined.

The following is an example of calculating a noisiness level or measure NOS for the segment score signal 1781. The calculations are performed in accordance with the method of FIG. 18A and equations 8-10:

$$m_1 = 1, m_2 = 0.9033$$

$$ratio = 0.9033, \quad dist = \frac{1291 - 118}{2000} = 0.5865$$

$$NOS = 0.5298$$

The noisiness measure NOS is larger than a predetermined threshold, e.g. 0.5 in this case, therefore the segment score signal 1781 may be determined as a noisy signal, and inappropriate for segmentation of the image stream. Other thresholds may be used to determine the noisiness of the segment score signal.

Figure 19:
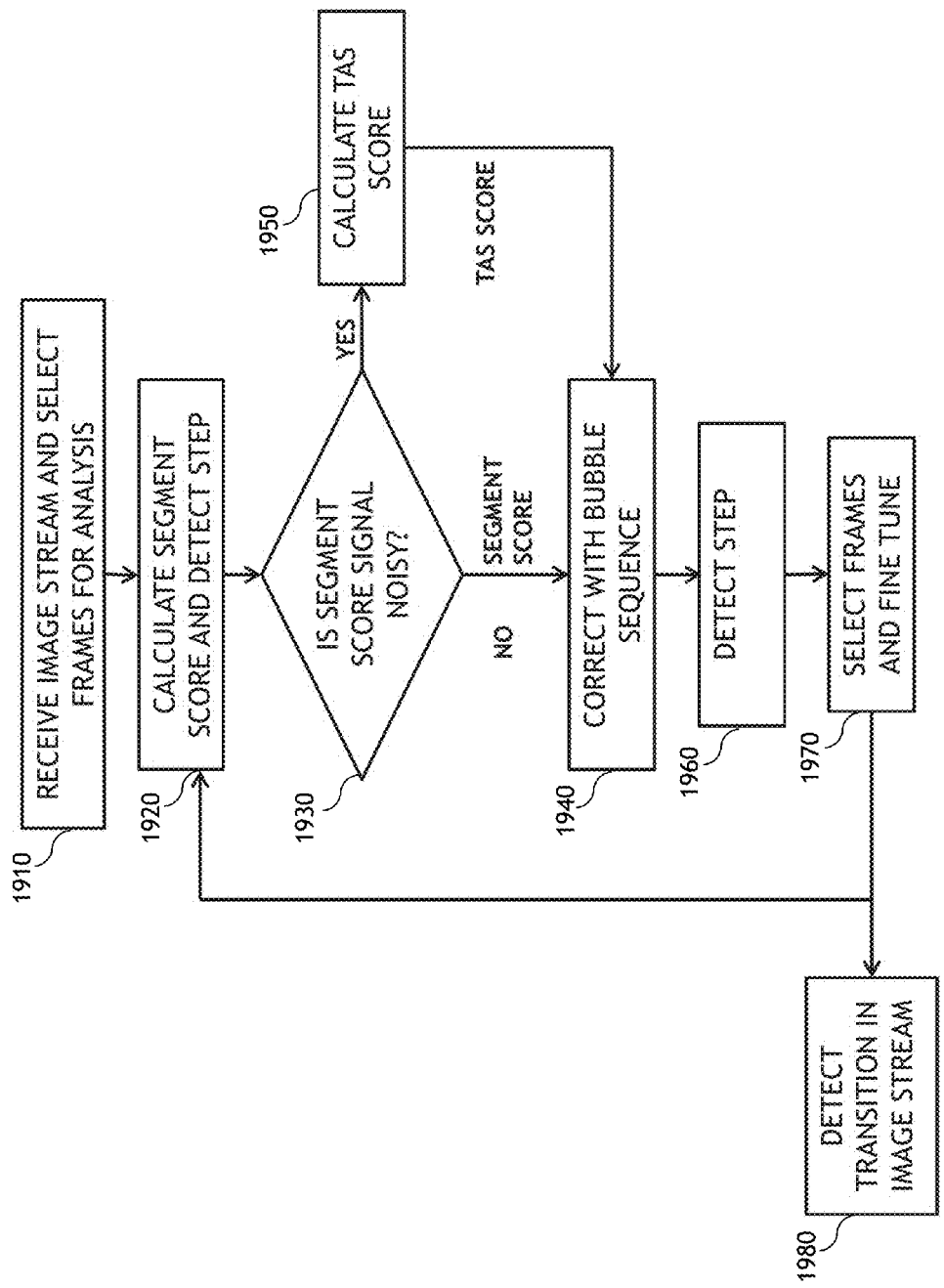
FIG. 19 is a flow chart of a method for detecting a transition in an image stream according to embodiments of the invention.

Reference is now made to FIG. 19, which includes a flow chart of a method for detecting a transition in an image stream according to embodiments of the invention. In operation 1910, a stream of in vivo images may be received and stored, for example by a receiver 12, which is operationally connected to data processor 15 and data processor storage unit 19. From the received stream of images, certain images may be selected for analysis or processing, e.g. as described with relation to operation 1015 of FIG. 9. In operation 1920, a segment score may be calculated for the image stream. The segment score may be calculated, for example, as described herein with relation to FIG. 9. Further, a step may be detected in the segment score signal according to embodiments described herein. The detected step may be a local step, a global step, or a combined step, e.g. as shown in operation 1165 and in eq. 4 and eq. 5. The detected step may represent, or may be correlated to, a point of transition in the image stream.

In operation 1930, a noisiness level or measure may be computed for the segment score signal, and according to a predetermined threshold, the segment score signal may be determined as a noisy or clean signal, e.g. as described in FIG. 18A.

If the segment score signal is determined as clean (or not noisy, e.g. having a low noisiness level), in operation 1940 a bubble sequence may be detected, e.g. as described in the flow chart of FIG. 16A. If a bubble sequence is detected, and if it overlaps or intersects with a low segment score sequence, then, in operation 1960, the detected segment score step (correlating to the point of transition of the image stream, which was detected based on the combined step) may be corrected, e.g. according to operations 1630-1645 of the flow chart of FIG. 16A.

Otherwise, if the segment score signal is determined to be noisy in operation 1930 (e.g. having a high noisiness level), a TAS score may be computed (e.g., calculated) in operation 1950 for the image stream or for selected images thereof, and a step may be detected in the TAS signal, e.g. according to operation 1720 of FIG. 17. In operation 1960, the detected TAS step may be corrected, e.g. similar to operations 1630-1645 of the flow chart of FIG. 16A. However, since the TAS function typically includes lower values in the small bowel and higher values in the colon, a high TAS sequence may be detected in the TAS function by detecting a first up-step and a subsequent down-step. In another embodiment, the TAS signal may be multiplied by (−1), and the operations 1630-1645 may be followed.

In operation 1970, the detected step of operation 1960 may be refined or fine-tuned. Since the original image stream was sampled at a predetermined sampling rate (e.g. 1 of 100 frames), and only the sampled images were selected for segmentation of the image stream, the detected step of operation 1960 may be quite far from the actual transition point in the image stream. For example, the original image stream may include 200,000 sequentially numbered images. Out of these, 2,000 (or another predetermined number) equally spaced frames throughout the stream may have been selected for segmentation analysis (e.g. in operation 1015 of FIG. 9). This creates a distance of 100 frames between consecutive selected image frames. Thus, the detected step of operation 1960 may be distanced up to 99 frames from the actual transition in the image stream.

In order to refine the detected step, a new subset of image frames may be selected from the original image stream. For example, the new subset may include a predetermined number of frames (or percentage of frames from the image stream) selected from the vicinity of the detected frame of the point of transition. In one example, if the detected step occurred at frame number 50,000 of the original image stream, 1,000 frames before (and/or after) the detected transition frame may be selected for a refining phase of the transition detection. Alternatively, a predetermined percent (e.g. 10%) of the frames from the vicinity of the detected point of transition in the image stream may be selected for the refining phase. The same operations which were performed for detecting a step or a transition frame in the initial sequence of selected frames for analysis, may be performed for the selected frames of the refined sequence, e.g. operations 1920-1960. After refining of the detected step, the refined transition frame in the image stream may be determined in operation 1980.

In some embodiments, other operations may be used to detect a transition in an image stream. It is noted that not all operations described herein must be performed in order to detect a transition in an image stream. In some embodiments, only a subset of the operations described herein may suffice for detecting the transition of an imaging device from one organ to another, or specifically from the small bowel to the colon.

In some embodiments, after detecting one transition in an image stream, the detected transition may be used to detect a next transition. For example, if a first transition from the stomach to the small bowel was detected in an image stream, the first transition may be used to verify that a second transition of the imaging device, e.g. from the small bowel to the colon, occurred at least a minimal amount of time from the first transition. For example, it may be known that physiologically, the transit time of a swallowable capsule through the small bowel, from the stomach to the colon, may take at least 15 minutes. Thus, if the first point of transition of the capsule from the stomach to the small bowel was determined to occur at a certain time, it may be verified, e.g. by a processing unit 15 or an anatomical detection unit 13, that at least 15 minutes passed from the detected first point of transition to the second point of transition. Other time periods or thresholds may be used, and other transitions may be determined. In some embodiments, images may be selected for processing according to transitions which were detected in the image stream. For example, a first point of transition between the gastric region to the small bowel may be determined, and images may be selected for determining the point of transition from the small bowel to the colon according to the first point of transition. E.g., only images which were captured at least a certain amount of time (e.g. 15 minutes or another predetermined time period) after the first point of transition may be selected for processing in operation 1910.

Once one or more points of transition are detected in an image stream, they may be used for several applications. For example, the images correlating to the points of transition may be suggested to a healthcare professional reviewing the image stream as landmark points in the image stream. A health care professional, such as a physician or nurse, may be interested in reviewing a certain anatomical region based on the suggested points of transition. The points of transition may be used in the detection of pathologies or other areas of interest (e.g. anatomical landmarks) in the image stream. In some embodiments, the points of transition may be used when generating a summarized or reduced movie for review by a health professional. For example, a predetermined number or percentage of images may be selected from each anatomical region detected by the anatomical region detector 13. If the health care professional is interested in the examining colon rather than other GI organs such as the small bowel or stomach, the point of transition from the small bowel to the colon may be used by a processor to select images for review or for a reduced image stream.

In some embodiments, if none of the scores mentioned above for determining the point of transition in an image stream are determined as reliable (e.g., in some cases, both the segment score and the TAS score may be too noisy for using in the determination of a transition point)—other methods may be used for determining or estimating a transition point. For example, the transition point from the small bowel to the colon may be determined as the frame captured a predetermined interval (e.g. 15 minutes) after the point of transition from the stomach to the small bowel. In another example, a point of transition may remain undetermined. A graphical indication may be displayed to a user, regarding an undetermined or unreliable result of the detection of the point of transition in the image stream. Embodiments of the invention may include an article such as a non-transitory computer or processor readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

The invention claimed is:

1. A computer-implemented method for detecting a transition in a stream of in-vivo images of a gastrointestinal (GI) tract, the method comprising:
   receiving an in-vivo image stream from an in vivo imaging device;
   selecting a subset of images from the image stream for analysis;
   calculating a segment score for each selected image, the segment score indicating in which anatomic segment of the GI tract the image was captured;
   applying a smoothing function on the segment scores of the selected images to obtain a smoothed segment score signal;
   detecting a global step in the smoothed segment score signal, said global step indicating a substantial change in a parameter calculated based on the segment score signal values;
   detecting a local step in the smoothed segment score signal, said local step indicating a substantial change in a parameter calculated based on segment score signal values of a predetermined interval of the selected images from the image stream;
   combining the local step and the global step to obtain a combined step; and
   determining a point of transition in the image stream from one anatomical segment to another, the point of transition correlating to the combined step.

2. The method of claim 1 comprising calculating a feature vector for each selected image, the feature vector based on: a villi score, the villi score corresponding to an amount of villi texture found in a selected image; a content score, the content score corresponding to the probability that the image depicts intestinal contents; and a white score, the white score corresponding to pixels in the image which are substantially white.

3. The method of claim 1 comprising:
   detecting a bubble sequence in the image stream, the bubble sequence corresponding to a sequence of images, wherein each image of the sequence contains at least a certain predetermined amount of bubbles; and
   determining a corrected point of transition according to the detected bubble sequence.

4. The method of claim 3 comprising:
   detecting a low segment score sequence, the low segment score sequence including a sequence of images which received a low segment score value relative to images in their vicinity;
   detecting an intersection of the bubble sequence and the low segment score sequence; and
   determining the middle of the bubble sequence as a corrected point of transition in the image stream.

5. The method of claim 1 wherein the transition in the image stream is from the small bowel to the colon.

6. The method of claim 1 comprising determining a noisiness level of the segment score signal, the noisiness level correlating to the reliability of the segment score signal for determining a point of transition in the image stream.

7. The method of claim 6 comprising, if the noisiness level of the segment score signal is above a predetermined threshold:
   calculating a tissue area score for each selected image to obtain a tissue area score signal, the tissue area score per image indicating an amount of tissue which is captured in an image;
   determining a step in the tissue area score signal; and
   determining the transition in the image stream according to the detected step in the tissue area score signal.

8. The method of claim 1 comprising refining the detected point of transition of the image stream by selecting a new subset of images from the image stream, the new subset selected from the vicinity of the detected point of transition.

9. A system for detecting a transition in a stream of in-vivo images of a gastrointestinal (GI) tract, the system comprising:
   a storage unit to store an in-vivo image stream received from an in vivo imaging device;
   a processor to:
   select a subset of images from the image stream for analysis;
   calculate a segment score for each selected image, the segment score indicating in which anatomic segment of the GI tract the image was captured;
   apply a smoothing function to the segment scores of the selected images to obtain a smoothed segment score signal;
   detect a global step in the smoothed segment score signal, said global step indicating an abrupt change in a parameter calculated based on the segment score signal values;
   detect a local step in the smoothed segment score signal, said local step indicating an abrupt change in a parameter calculated based on segment score signal values of a predetermined interval of the selected images from the image stream;
   combine the local step and the global step to obtain a combined step; and
   determine a transition in the image stream from one anatomical segment to another, the point of transition correlating to the combined step.

10. The system of claim 9, wherein the processor is to calculate a feature vector for each selected image, the feature vector based on: a villi score, the villi score corresponding to an amount of villi texture found in a selected image; a content score, the content score corresponding to the probability that the pixel depicts intestinal contents; and a white score, the white score indicating pixels values which are substantially white.

11. The system of claim 9, wherein the processor is to detect a bubble sequence in the image stream, the bubble sequence corresponding to a sequence of images, wherein each image of the sequence contains at least a certain predetermined amount of bubbles; and to correct the point of transition according to the detected bubble sequence.

12. The system of claim 11, wherein the processor is to: detect a low segment score sequence, detect an intersection of the bubble sequence and the low segment score sequence; and determine the middle of the bubble sequence as a corrected point of transition in the image stream.

13. The system of claim 9, wherein the transition in the image stream is from the small bowel to the colon.

14. The system of claim 9, wherein the processor is to determine a noisiness level of the segment score signal.

15. The system of claim 9, wherein if the noisiness level of the segment score signal is above a predetermined threshold, the processor is to:

calculate a tissue area score for each selected image to obtain a tissue area score signal, the tissue area score per image indicating an amount of tissue which is captured in an image;

determine a step in the tissue area score signal; and determine the transition in the image stream according to the detected step in the tissue area score signal.

16. The system of claim 9, wherein the processor is to refine the detected point of transition of the image stream by selecting a new subset of images from the image stream, the new subset selected from the vicinity of the detected point of transition.

17. The system of claim 9, wherein the abrupt change in the parameter calculated based on the segment score signal values is a maximal detected change.

18. A method for detecting a transition in a stream of in-vivo images of a gastrointestinal (GI) tract, the method comprising:

selecting images from an in-vivo image stream;

calculating a rating for each selected image, the rating indicating a probability that the image was captured in a predetermined anatomic segment of the GI tract;

applying a smoothing function on the ratings of the selected images to obtain a rating function;

detecting a global increment in the smoothed segment score signal indicating a maximal change in a parameter calculated based on the segment score signal values;

detecting a local increment in the smoothed segment score signal indicating a maximal change in a parameter calculated based on a predetermined window of the of the segment score signal values;

determining a point of transition in the image stream from one anatomical segment based on a combination of the local increment and the global increment.

19. The method of claim 18 comprising calculating a feature vector for each selected image, the feature vector based on: a villi score, the villi score corresponding to an amount of villi texture found in a selected image; a content score, the content score corresponding to the probability that the image depicts intestinal contents; and a white score, the white score corresponding to pixels in the image which are substantially white.

20. The method of claim 19 comprising:

detecting a bubble sequence in the image stream, the bubble sequence corresponding to a sequence of images, wherein each image of the sequence contains at least a certain predetermined amount of bubbles; and determining a corrected point of transition according to the detected bubble sequence.

* * * * *